(12) United States Patent
Marcelpoil

(10) Patent No.: US 11,319,575 B2
(45) Date of Patent: May 3, 2022

(54) METHODS AND SYSTEMS FOR AUTOMATED ASSESSMENT OF ANTIBIOTIC SENSITIVITY

(71) Applicant: BD KIESTRA B.V., Drachten (NL)

(72) Inventor: Raphael Rodolphe Marcelpoil, Corenc (FR)

(73) Assignee: BD KIESTRA B.V., Drachten (NL)

( * ) Notice: Subject to any disclaimer, the term of this patent is extended or adjusted under 35 U.S.C. 154(b) by 88 days.

(21) Appl. No.: 16/650,087

(22) PCT Filed: Sep. 27, 2018

(86) PCT No.: PCT/EP2018/076257
§ 371 (c)(1),
(2) Date: Mar. 24, 2020

(87) PCT Pub. No.: WO2019/063690
PCT Pub. Date: Apr. 4, 2019

(65) Prior Publication Data
US 2020/0291447 A1 Sep. 17, 2020

Related U.S. Application Data

(60) Provisional application No. 62/564,727, filed on Sep. 28, 2017.

(51) Int. Cl.
*C12Q 1/18* (2006.01)
*C12Q 1/20* (2006.01)
(Continued)

(52) U.S. Cl.
CPC ............... *C12Q 1/18* (2013.01); *C12Q 1/20* (2013.01); *G01N 21/17* (2013.01); *G06K 9/0014* (2013.01);
(Continued)

(58) Field of Classification Search
CPC .......... C12Q 1/18; C12Q 1/20; G06K 9/0014; G06K 9/00127; G06K 9/00134;
(Continued)

(56) References Cited

U.S. PATENT DOCUMENTS 6,153,400 A * 11/2000 Matsumura ............... C12Q 1/18
435/283.1
6,472,166 B1 * 10/2002 Wardlaw ................... C12Q 1/18
435/32
(Continued)

FOREIGN PATENT DOCUMENTS

WO 2015114121 A1 8/2015

OTHER PUBLICATIONS

An Automated System for Rapid Non-Destructive Enumeration of Growing Microbes (Year: 2010).*
(Continued)

*Primary Examiner* — Nizar N Sivji
(74) *Attorney, Agent, or Firm* — Botos Churchill IP Law LLP

(57) ABSTRACT

An imaging system and method provides automated microbial growth detection for antibiotic sensitivity testing. A processing system having an image sensor for capturing images of an inoculated culture plate having antibiotic disks disposed on the culture media captures images of the plate at separate times (e.g., first and second images). The system generates pixel characteristic data for pixels of the second image from a comparison of the first image and second image. The pixel characteristic data may be indicative of plate growth. The system may access growth modeling data concerning the antibiotic disk(s) and generate simulated image data with a growth model function. The growth model function uses the growth modeling data. The simulated image data simulates growth on the plate relative to the
(Continued)

disk(s). The system compares the simulated image and the pixel characteristic data to identify pixel region(s) of the second image that differ from the simulated image.

25 Claims, 19 Drawing Sheets

(51) Int. Cl.
    *G06K 9/00*     (2006.01)
    *G06T 7/11*     (2017.01)
    *G01N 21/17*     (2006.01)
    *G06T 7/00*     (2017.01)
    *G06T 7/90*     (2017.01)

(52) U.S. Cl.
    CPC ..... *G06K 9/00127* (2013.01); *G06K 9/00134* (2013.01); *G06T 7/0016* (2013.01); *G06T 7/11* (2017.01); *G06T 7/90* (2017.01)

(58) Field of Classification Search
    CPC ............... G01N 21/17; G01N 21/6428; G01N 21/6458; G01N 2333/71; G01N 33/582; G01N 33/5026; G01N 33/6803; G06T 7/11; G06T 2207/10064; G06T 7/0012; G06T 7/0016; G06T 7/70
    See application file for complete search history.

(56) References Cited

U.S. PATENT DOCUMENTS

| | | | |
|---|---|---|---|
| 10,921,336 B2* | 2/2021 | Hansen | C12Q 1/04 |
| 2001/0039032 A1* | 11/2001 | Matsumura | C12Q 1/04 |
| | | | 435/32 |
| 2007/0037225 A1* | 2/2007 | Metzger | G01N 33/5438 |
| | | | 435/7.22 |
| 2014/0278136 A1* | 9/2014 | Shamsheyeva | B01L 3/502715 |
| | | | 702/19 |
| 2015/0299639 A1 | 10/2015 | Kleefstra | |
| 2017/0350805 A1* | 12/2017 | Murata | C12M 1/34 |
| 2018/0112173 A1* | 4/2018 | Wiles | G06T 7/0016 |
| 2019/0144525 A1* | 5/2019 | Muraya | C12N 5/0018 |
| | | | 435/69.1 |
| 2020/0110923 A1* | 4/2020 | Tanikawa | G06K 9/00127 |

OTHER PUBLICATIONS

Annals of Clinical Microbiology and Antimicrobials (Year: 2007).*
Miniaturized Antimicrobial Susceptibility Test by Combining Concentration Gradient Generation and Rapid Cell Culturing (Year: 2015).*
Office Action issued in corresponding European Patent Application No. 18782365.3 dated Apr. 20, 2021, 5 pp.
Brigitte Lamy et al.: "How does susceptibility prevalence impact on the performance of disk diffusion susceptibility testing?", Diagnostic Microbiology and Infectious Disease, vol. 49, No. 2, Jun. 1, 2004 (Jun. 1, 2004), pp. 131-139, XP55529975.
PCT International Search Report issued in PCT application No. PCT/EP2018/076257 dated Dec. 13, 2018.
Mathieu Daynac et al.: "Application of Artificial Intelligence to the Prediction of the Antimicrobial Activity of Essential Oils", Evidence-Based Complementary and Alternative Medicine, vol. 2015, Jan. 1, 2015 (Jan. 1, 2015), XP55530015, pp. 1-9.
Bruce A. Craig et al: "Modeling approach to diameter breakpoint determination", Diagnostic Microbiology and Infectious Disease, vol. 36, No. 3, Mar. 1, 2000 (Mar. 1, 2000), XP55530006, pp. 193-202.
Bhargav HS et al.: "Measurement of the Zone of Inhibition of an Antibiotic", 2016 IEEE 6th International Conference on Advanced Computing (IACC), IEEE, Feb. 27, 2016 (Feb. 27, 2016), XP032945454, pp. 409-414.
Hejblum G. et al.: "Automated Interpretation of Disk Diffusion Antibiotic Susceptibility Tests With the Radia Profile Analysis Algorith", Journal of Clinical Microbiology, American Society for Microbiology, US, vol. 31, No. 9, XP00064684, (Sep. 1, 1993), pp. 2396-2401.

* cited by examiner

ENTEROCOCCUS FAECIUM, ENTEROCOCCUS GALLINARUM & LEUCONOSTOC
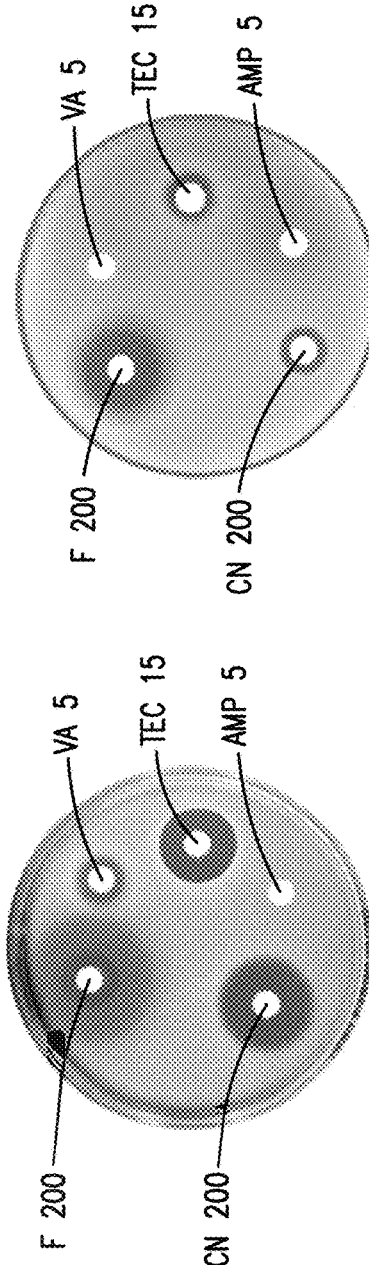
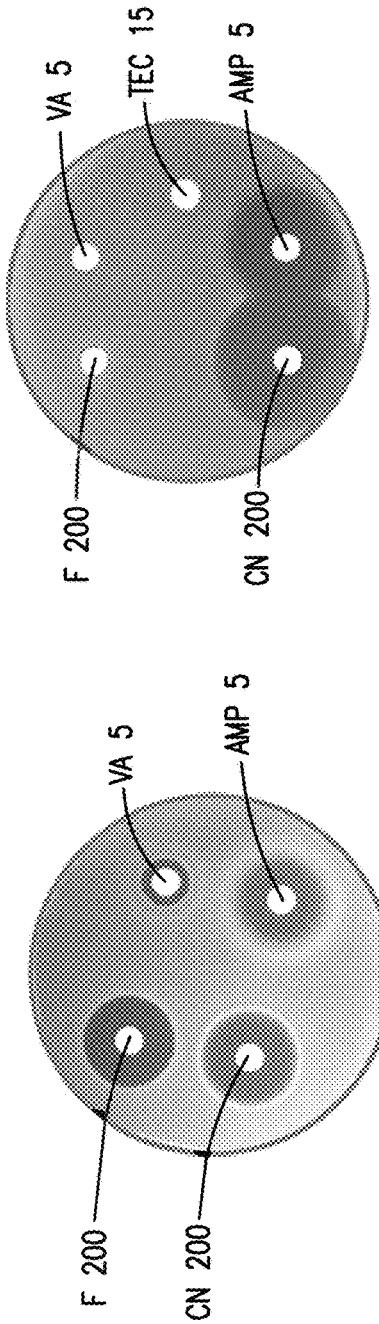
FIG. 17

PATTERN WHEN ANTIBIOTIC DISK CAUSES NO GROWTH MODULATION

GROWTH MODULATION CAUSED BY A SINGLE DISK

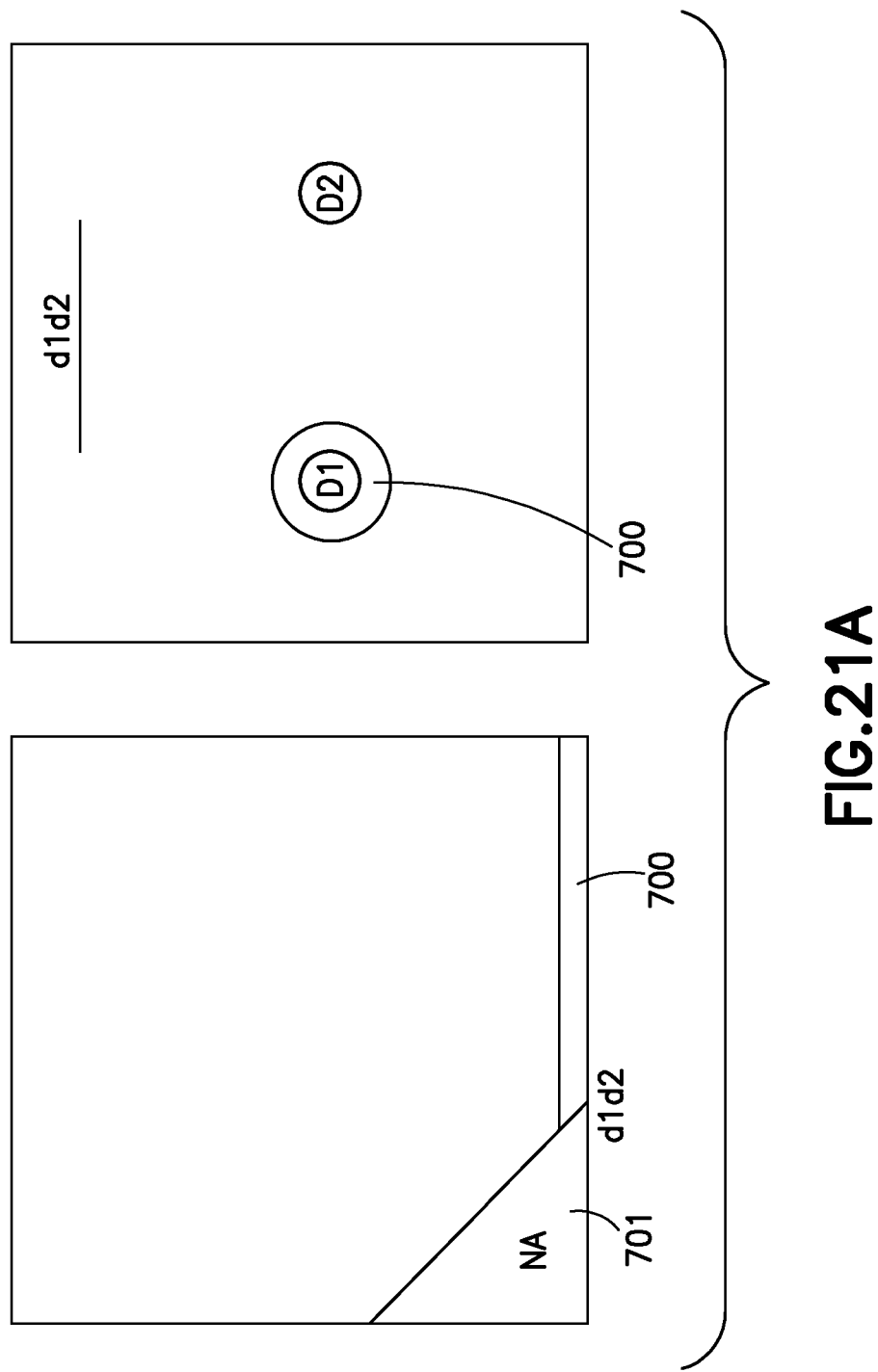

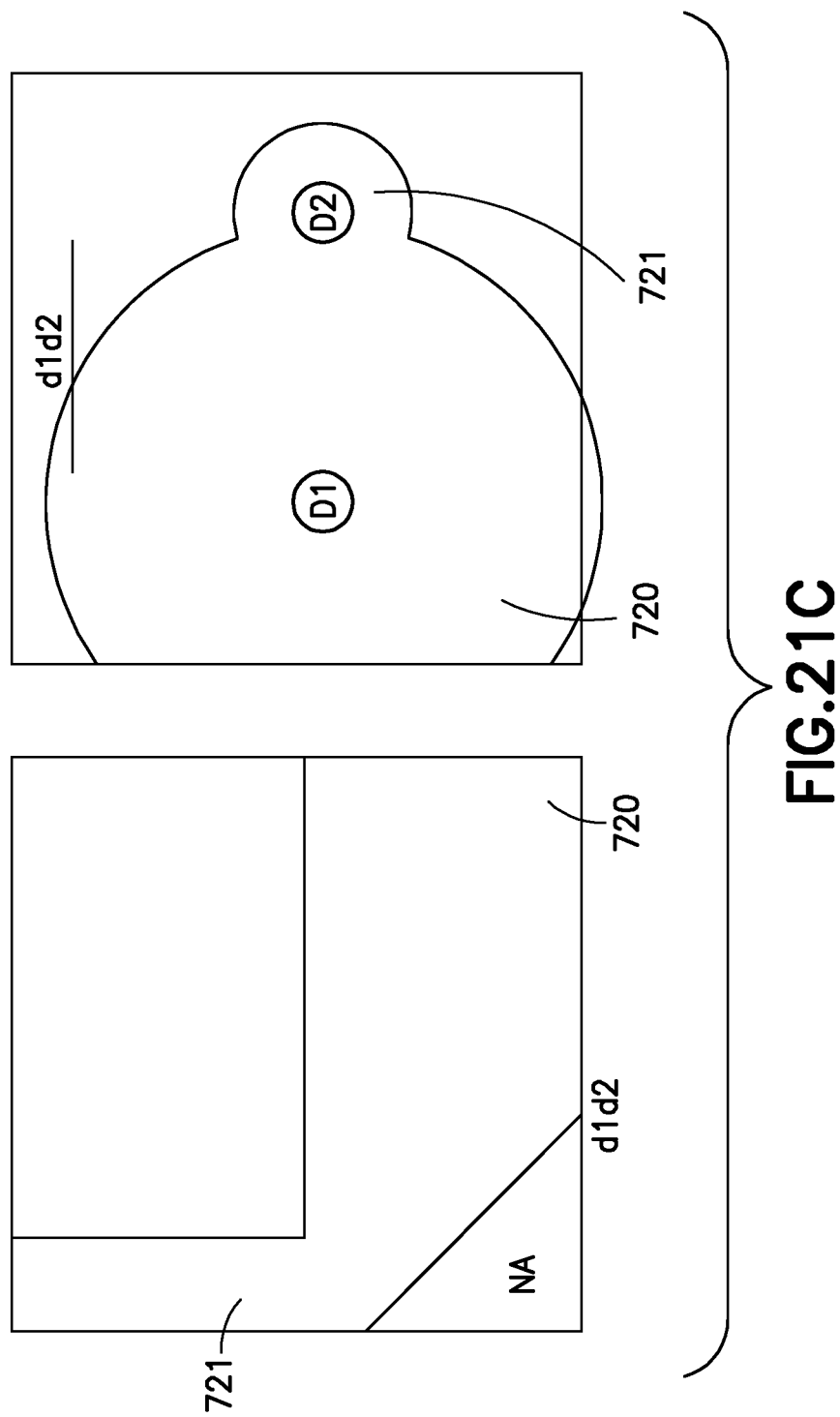

METHODS AND SYSTEMS FOR AUTOMATED ASSESSMENT OF ANTIBIOTIC SENSITIVITY

CROSS-REFERENCE TO RELATED APPLICATIONS

The present application is a national phase entry under 35 U.S.C. § 371 of International Application No. PCT/EP2018/076527, filed Sep. 27, 2018, which claims the benefit of the filing date of U.S. Provisional Patent Application No. 62/564,727, filed Sep. 28, 2017, the disclosures of which are hereby incorporated by reference herein.

BACKGROUND OF THE TECHNOLOGY

There is increased focus on digital imagery of culture plates for detection of microbial growth. Techniques for imaging plates for detecting microbial growth are described in PCT Publication No. WO2015/114121, the entirety of which is incorporated by reference herein. Using such techniques, laboratory staff is no longer required to read plates by direct visual inspection but can use high quality digital images for plate inspection. Shifting laboratory workflow and decision-making to examination of digital images of culture plates can also improve efficiency. Images can be marked by an operator for further work-up by either the operator or another person with the appropriate skills. Additional images may also be taken and used to guide secondary processes.

For example, imaging may be utilized for agar diffusion testing. In agar diffusion testing, the sensitivity of bacteria microorganism to antibiotics is determined. Such testing, which may be referred to as Antibiotic Sensitivity Testing (AST), typically involves application of several antibiotic disks to a medium (e.g., agar) on a plate that has been spread evenly with a bacterium to be tested. Different disks may have different concentrations of a particular antibiotic and/or several different antibiotics. The plate may be incubated to permit growth time for the bacteria. The plate is then viewed. The bacterial growth in the area around each antibiotic disk provides an indication of the effect of the particular antibiotic of the disk. For example, an effective antibiotic of a particular disk may have a large area that is free of growth of the tested bacteria whereas an ineffective antibiotic of a particular disk may have no area free of growth of the tested bacteria.

The size of the growth-free zone can provide an indication as to a minimum inhibitory concentration of the antibiotic of a nearby disk. For example, in the case of agar, after a disk is placed, the antibiotic will migrate away from the disk over time. The migration will diffuse the antibiotic concentration according to the distance from the disk and the rate of diffusion for the antibiotic and medium. The antibiotic concentration will be highest near the disk. The concentration will decrease at further distances from the disk. Typically, the minimum inhibitory concentration can be considered the lowest concentration furthest from to the disk that includes an absence of bacterial growth.

Such determinations may then help for selecting suitable antibiotics and their doses for different bacterial infections. This helps to define the objectives for a modern microbiology imaging system. Having these objectives realized as early as possible achieves the goals of delivering results to a patient quickly and providing such results and analysis economically. Automating laboratory workflow and decision-making can improve the speed and cost at which these goals may be achieved.

Although considerable progress has been made regarding imaging technologies for detecting evidence of microbial growth, it is still sought to extend such imaging technologies to support an automated workflow. Apparatus and methods for inspecting culture plates for indications of microbial growth are difficult to automate, due in part to the highly visual nature of plate inspection. In this regard, it is desirable to develop techniques that may automate interpretation of culture plate images (e.g., identification of growth, susceptibility testing, antibiotic sensitivity analysis etc.) and determine the next steps to be performed based on the automated interpretation.

BRIEF SUMMARY OF THE TECHNOLOGY

An aspect of the present disclosure is directed to a method in a processor for antibiotic susceptibility testing. In the method, a culture plate inoculated with a biological sample is provided. The culture plate has culture media and at least one antibiotic disk disposed thereon. First and second image data of the culture plate is generated with an image sensor. The first image data and second image data respectively represent first and second captured images of the culture plate. The first and second captured images taken at separate times using image sensors. The image sensors are controlled to collect the desired image information (i.e. color, intensity, etc.). Pixel characteristic data is generated for pixels of the second image data from a comparison of the first image data and the second image data. The pixel characteristic data is indicative of microbial growth on the culture plate over time. Modeling data for microbial growth is then accessed. The modeling data models microbial growth for combinations of culture media, microorganisms, antibiotic, antibiotic concentration on the disk and in the culture media. The antibiotic concentration in the culture media is a function of antibiotic concentration on the disk, time and the distance from the disk. Simulated image data is generated using a growth model function. The simulated image data simulates microbial growth on the inoculated culture plate based on the at least one disk of the plurality of antibiotic disks disposed on the culture media, the antibiotic concentration on the at least one disk; the culture media and the concentration of the antibiotic in the culture media as a function of time and distance from the antibiotic disk. The simulated image data and the pixel characteristic data are compares and one or more pixel regions of the second image data that differ from one or more pixel regions of the simulated image data are identified.

One example of pixel characteristic data is contrast data. Contrast data can be pixel intensity values. Contrast data can include opacity data, color data and blurring data.

Pixel characteristic data can also include distance data, the distance data representing distance to the at least one of the plurality of antibiotic disks. For example, distance data is a distance from the pixel to the center of the at least one of the plurality of antibiotic disks.

The growth model function can model one or more of maximum growth, minimum growth, average growth, a median growth or percentile growth. In one example, the growth model function characterizes contrast data as a function of radial distance from the at least one disk of the plurality of antibiotic disks. The growth model function can include a diffusion map for diffusion of the antibiotic into the culture media.

The method can include the steps of detecting in the first image data or second image data the image of the disk itself, and analyzing the disk image data to detect indicia data. Accessing growth modeling data can include locating the growth modelling data using the indicia data. The growth modelling data can include concentration information for an antibiotic load of the at least one disk of the plurality of antibiotic disks.

In one example, the growth model function uses one or more of: i) a growth time parameter representing elapsed time for growth of the growth plate at a time of capture of the second image data; ii) a diffusion coefficient parameter; and iii) a dimensionality parameter.

In one example the generated simulated image data includes an image mask having first image pixels representing a no-growth zone corresponding with a location of the at least one disk of the plurality of antibiotic disks in the growth plate and second image pixels representing a growth zone radiating from the no-growth zone and beginning at a radial distance from the location, the radial distance determined from the growth model function, the radial distance representing an estimated inhibition zone limit for the at least one disk.

When comparing the simulated image data and the pixel characteristic data, contrast between the pixels in the image mask and the pixel characteristic data is used to generate difference image data. A region of the second image data is then evaluated based on the difference image data. For temporal contrast (i.e. a difference in pixel intensity over time), the first image data can serve as a pre-growth reference for growth.

In one embodiment, the method is practiced by a computer. Specifically, instructions executed by the processor can be used to perform the method described above.

Also described herein is a system for antibiotic susceptibility testing. The system includes an image sensor configured to capture images of a culture plate on which is disposed culture media with at least one antibiotic disk disposed thereon. The culture plate is inoculated with a biological sample wherein the culture plate is within a field of view of the image sensor. The system includes a processor coupled with the image sensor. The system also includes a computer medium containing programming instructions that, when executed by the processor, control the processor for testing antibiotic susceptibility. For example, the program instructions control the processor to perform the method described herein.

In another embodiment, the system includes an image sensor configured to capture images of a culture plate on which is disposed culture media with a plurality least one antibiotic disk disposed thereon. The culture plate is inoculated with a biological sample when the culture plate is within a field of view of the image sensor, the image sensor generating first image data and second image data, the first image data and second image data respectively representing first and second captured images of the culture plate including the plurality of antibiotic disks, the first and second captured images taken at respective first and second times. The system includes a processor and a memory. The processor receives the first image data and second image data and accesses the memory. The memory stores the growth modeling data. The processor generates pixel characteristic data for pixels of the second image data based on a comparison of the first image data and the second image data. The pixel characteristic data is indicative of microbial growth on the culture plate. The processor also accesses growth modeling data. The growth modelling data models microbial growth as a function of culture media, microorganism, antibiotic and antibiotic concentration. The processor also generates simulated image data with a growth model function, the growth model function using the growth modeling data, the simulated image data simulating microbial growth on the culture plate in relation to the at least one disk of the plurality of antibiotic disks. The processor then compares the simulated image data and the pixel characteristic data to identify one or more pixel regions of the second image data that differ from the simulated image data.

BRIEF DESCRIPTION OF THE DRAWINGS

FIG. 17 illustrates examples of inhibitory zones formed around antibiotic disks for the bacteria *Enterococcus faecium, Enterococcus gallinarum* and *Leuconstoc*.

FIGS. 21A-F illustrate transforms of growth modulation caused by one or more antibiotic disks to two dimensional representations of modulation as a function of distance from each of two disks.

DETAILED DESCRIPTION

The present disclosure provides apparatus and methods for identifying and analyzing microbial growth for antibiotic susceptibility testing on plated media. Many of the methods described herein can be fully or partially automated, such as being integrated as part of a fully or partially automated laboratory workflow.

The systems described herein are capable of being implemented in optical systems for imaging microbiology samples. There are many such commercially available systems, which are not described in detail herein. One example is the BD Kiestra™ ReadA Compact intelligent incubation and imaging system. Other example systems include those described in PCT Publication No. WO2015/114121 and U.S. Patent Publication 2015/0299639, the entirety of which is incorporated by reference herein. Such optical imaging platforms are well known to those skilled in the art and not described in detail herein.

Figure 1:
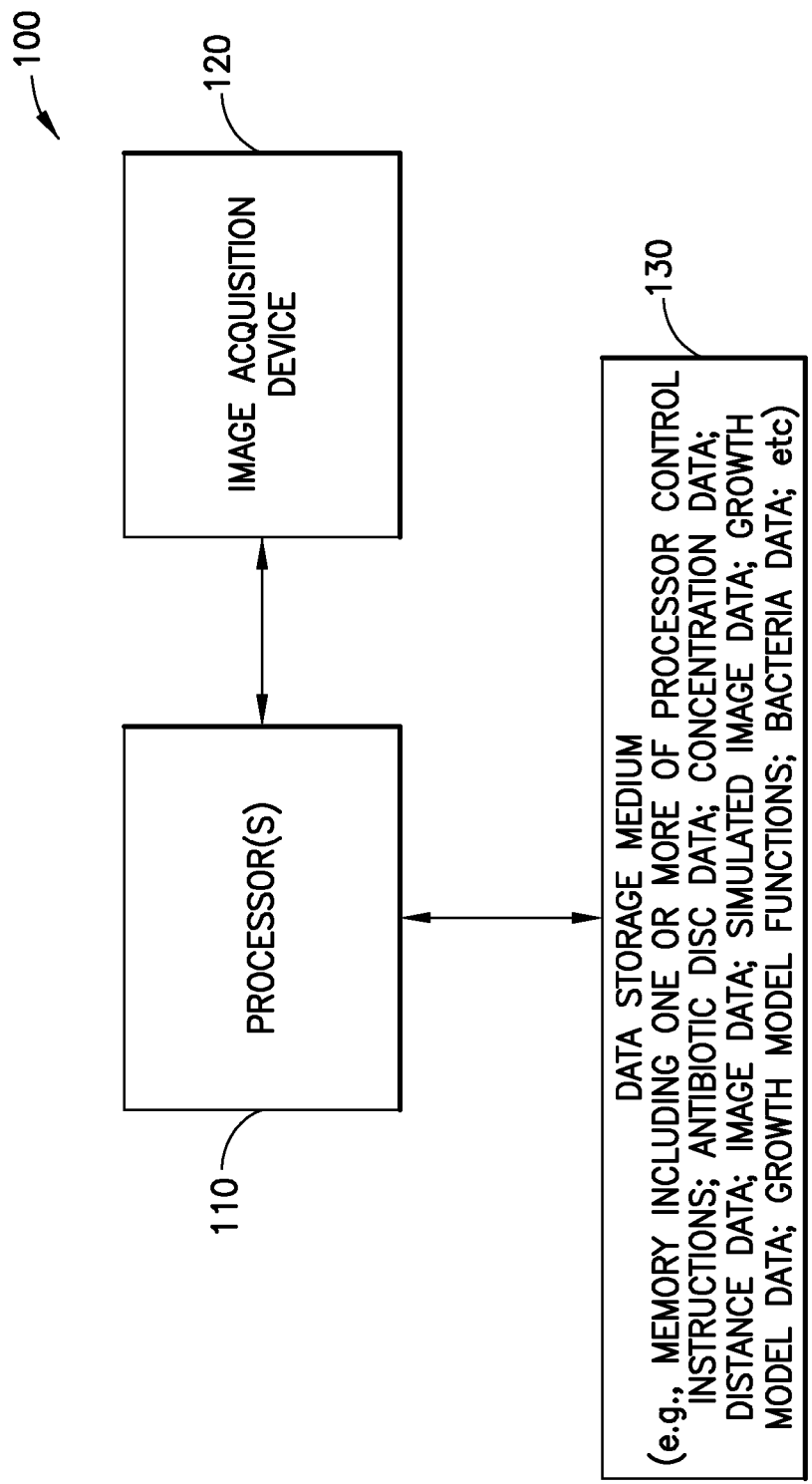
FIG. 1 is a schematic diagram of an example system for image based antibiotic susceptibility testing according to an aspect of the disclosure.

FIG. 1 is a schematic of an example antibiotic susceptibility testing system 100 having a processing module 110 and image acquisition device 120 (e.g., camera) for providing high quality imaging of plated media. The system will also typically have access to a data storage medium 130, such as one or more data memories, where such memories may include, for example, processor control instructions for controlling a processor to carry out any of the processes or methods described herein. The memory may also include antibiotic disk data; antibiotic concentration data; distance data; image data; simulated image data, growth model data; growth model functions; bacteria data, etc. The processing module and image acquisition device may be further connected to, and thereby further interact with, other system components, such as an incubation module (not shown) for incubating the plated media to allow growth of a culture inoculated on the plated media. Such connection may be fully or partially automated using a track system that receives specimens for incubation and transports them to the incubator, and then between the incubator and image acquisition device.

The processing module 110 may instruct the other components of the system 100 to perform tasks based on the processing of several types of information. The processor 110 may be hardware that performs one or more operations. The processor 110 may be any standard processor, such as a central processing unit (CPU), or may be a dedicated processor, such as an application-specific integrated circuit (ASIC) or a field programmable gate array (FPGA). While one processor block is shown, the system 100 may also include multiple processors which may or may not operate in parallel, or other dedicated logic and memory for storing and tracking information related to the sample containers or AST plates in the incubator and/or image acquisition device 120. In this regard, the processing unit may track and/or store several types of information regarding an AST plate in the system 100, including but not limited to the location of the AST plate in the system (incubator or image acquisition device, locations and/or orientation therein, etc.), the incubation time, pixel information of captured images, the type of AST plate (e.g., antibiotic(s) concentration(s) and bacteria type) sample, the type of culture media, precautionary handling information (e.g., hazardous specimens), etc. In this regard, the processor may be capable of fully or partially automating the various routines described herein. In one embodiment, processor control instructions for controlling the routines described herein may be stored on a non-transitory computer-readable medium (e.g., a software program).

Figure 2:
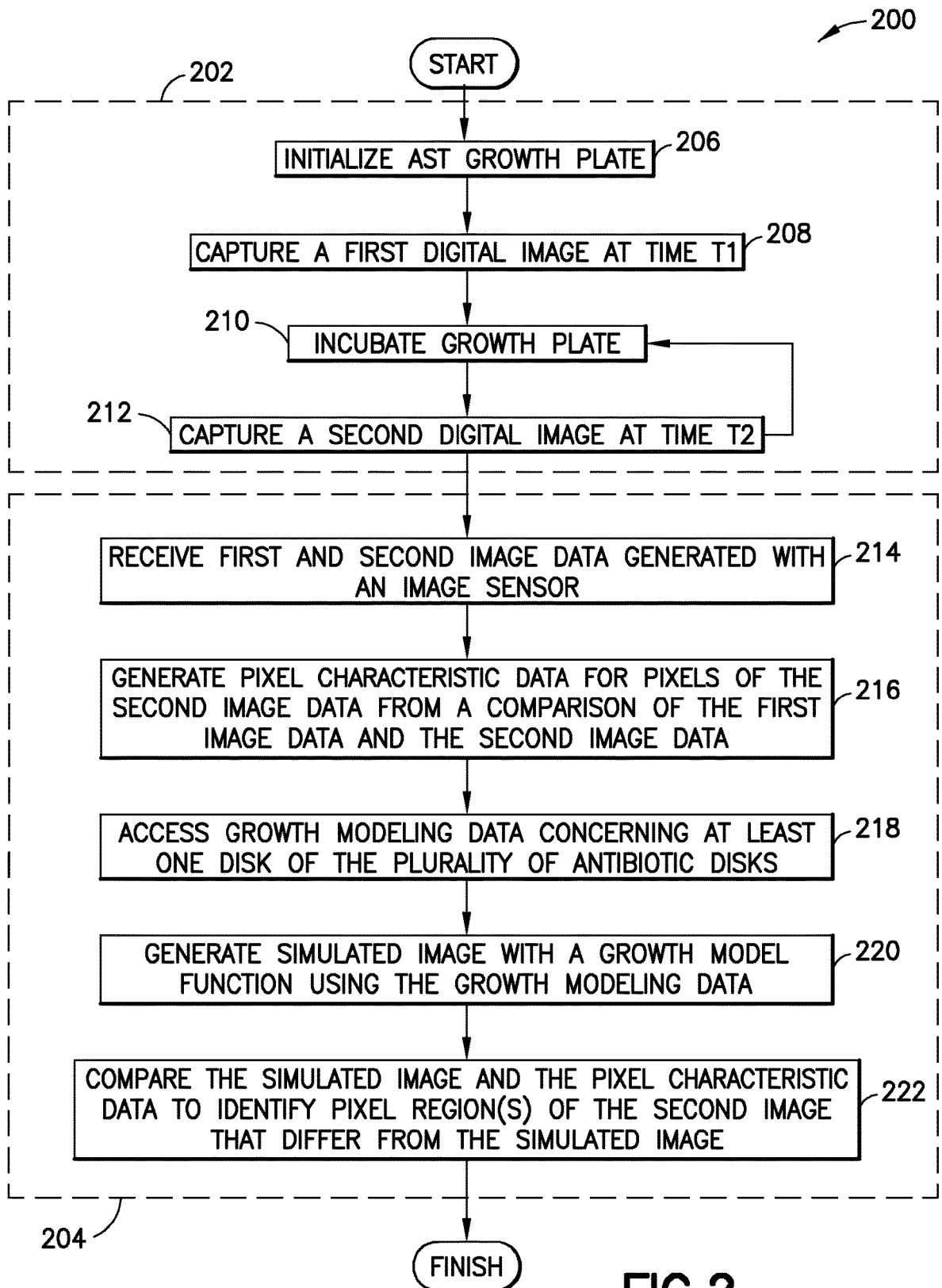
FIG. 2 is a flow chart illustrating an example automated process for image based antibiotic susceptibility testing according to an aspect of the disclosure.

FIG. 2 is a flow chart showing an example automated laboratory routine 200 for conducting antibiotic sensitivity testing. The routine 200 may be implemented by an automated microbiology laboratory system, such as the Kiestra™ Total Lab Automation or Kiestra™ Work Cell Automation, both manufactured by Becton, Dickenson & Co. The example systems include interconnected modules, each module configured to execute one or more steps of the routine 200. In the example, the routine 200 may be understood to include a growth and imaging process 202 and an image assessment process 204.

Growth and Imaging Process 202

At 206, a culture plate, such with an agar medium, is prepared for AST. The culture plate, or other suitable container, is provided and inoculated with a biological sample (e.g., a bacterium). The culture plate may be an optically transparent container, such that the biological sample and antibiotic disks may be observed in the container while illuminated from various angles. Inoculation may follow a predetermined pattern or process to uniformly apply the bacterium to the medium. Automated methods for inoculating the plate are well known to one skilled in the art. At 206, one or more antibiotic samples, e.g., an antibiotic wafer such as in a disk shape, are applied to the medium.

At 208, a first digital image may be captured by the image sensor of the system. Preferably, such an image will be captured at or near the time of culture plate initialization before any growth.

At 210, the medium is incubated to allow for growth of the biological sample.

At 212, a further digital image (one or more) of the medium and biological sample may then be captured, such as at a predetermined time relative to the initialization of the AST plate. Digital imaging of the medium may be performed multiple times during the incubation process (e.g., at the start of incubation, at a time in the middle of incubation, at the end of incubation) so that changes in the medium may be observed and analyzed. The timing may be based on the nature of the AST plate such as the type and concentration of the antibiotic(s) being tested. Imaging of the medium may involve removing the medium from the incubator. Where multiple images are taken of the medium after different incubation times, the medium may be returned to the incubator for further incubation between imaging sessions.

Image Assessment Process 204

After imaging, the AST plate is analyzed based on information from the captured digital image(s). Analysis of the digital image may involve analysis of pixel information contained in the image(s). In some instances, pixel information may be analyzed on a pixel-by-pixel basis. In other instances, pixel information may be analyzed on a block by block basis. In yet further instances, pixels may be analyzed based on entire regions of pixels, whereby the pixel information of individual pixels in the region may be derived by combining information of the individual pixels, selecting sample pixels, or by using other statistical methods such as the statistical histogram operations described in greater detail below. In the present disclosure, operations that are described as being applied to "pixels" are similarly applicable to blocks or other groupings of pixels, and the term "pixel" is hereby intended to include such applications Typically, the analysis may involve determining whether a growth (or an absence of growth) is detected in relation to the antibiotic disks of the medium. From an image analysis perspective, growth can be detected in an image by identifying an imaged object (based on differences between the object and its adjacent surroundings) and then identifying changes in the object over time. As described in greater detail herein, these differences and changes are both forms of "contrast." Contrast may be represented, such as on a pixel-by-pixel basis, by any one or more of intensity value, color value(s), grey value, opacity value and blurring value.

Figure 4:
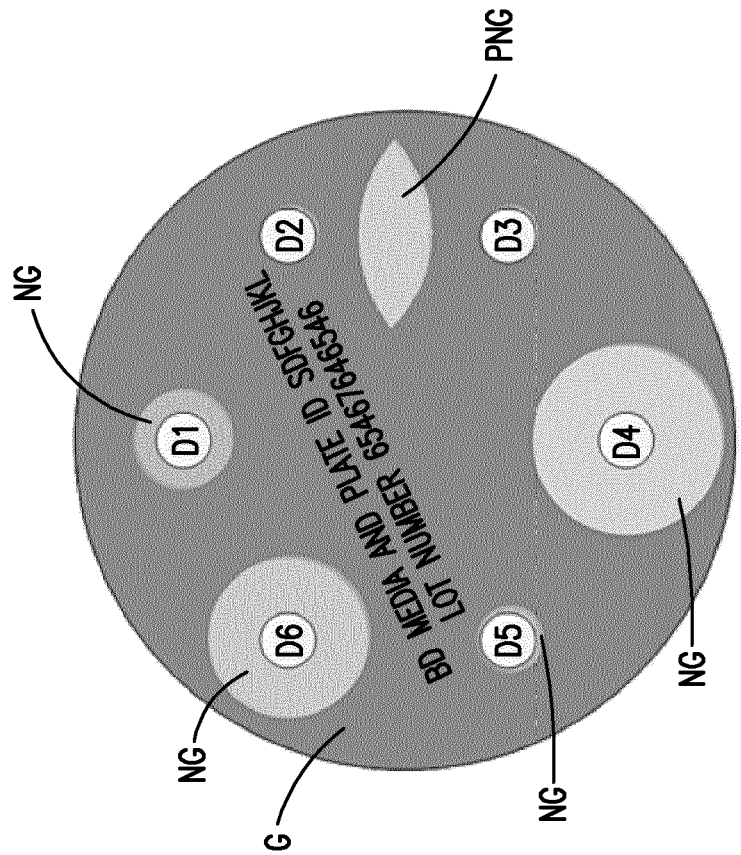
FIG. 4 is an illustration of an image of a growth plate, such as the growth plate of FIG. 3, having antibiotic disks and showing the plate after incubation and/or significant growth time where bacterial growth has occurred.
Figure 3:
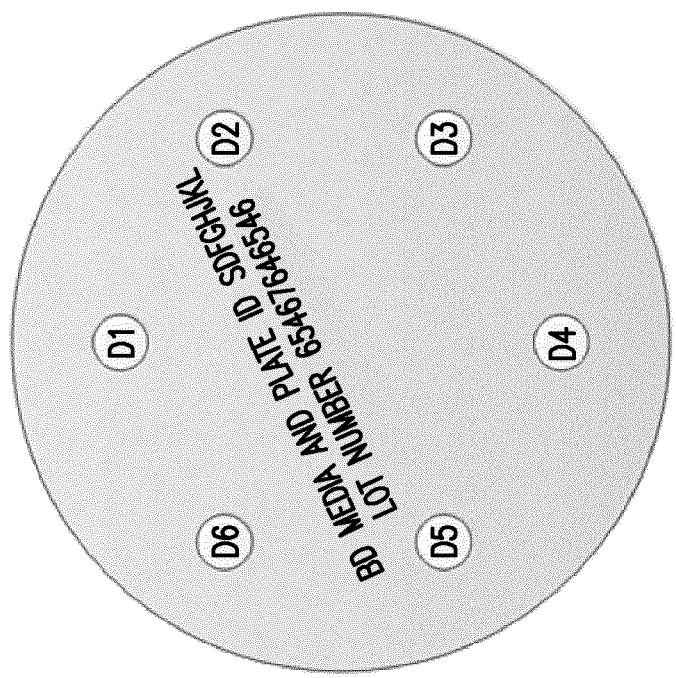
FIG. 3 is an illustration of an image of a growth plate having antibiotic disks showing the plate before incubation and/or without any significant growth time.

For example, at 214, data representing first and second captured images of a particular plate may be received in a processor. The first and second images are taken at separate times where the "first" image will be understood to be an image taken of the plate before the second image but is not necessarily the immediately preceding image taken of the plate before the second image. Other images of the plate may be taken between the first and second images. Typically, there will be some significant incubation time between the first and second images. (See, e.g., FIG. 4 showing the disk of FIG. 3 having growth G after incubation but with no growth NG around disks D1, D4, D5 and D6 and partial no growth PNG around D3 and D2.) In some cases, the first image may be a pre-incubation image, such as an image taken at process 208 (See, e.g., FIG. 3 showing disks D1-D6 and no growth on the plate image). In some cases, the first image may be an image taken after at least some incubation time, such as in process 212.

At 216, the processor may generate pixel characteristic data for pixels of the second image from a contrast analysis that involves a comparison of the first image data and the second image data. As described in more detail herein, this may involve a comparison of first image data (e.g., serving as background properties) and the second image data to evaluate growth level achieved in the second image data. For example, by disregarding the antibiotic disk in the images, the pixel characteristic data may represent an indication of the most different homogenous plate regions of a recent image when compared to a prior image (e.g., pre-incubation image).

Optionally, such a comparison may also be made on a region-by-region basis such as in relation to each antibiotic disk on the plate. Such a process may involve detection of particular region(s) of the image by detection of an antibiotic disk and/or a marking of the antibiotic disk. This may optionally involve evaluation of a normalized version of the image. For example, the processor may scan the first and/or second image, or a normalized version thereof, by performing character recognition of a marker on the antibiotic disks. Recognized characters of the markers may serve as an index for accessing a memory, such as a database, that includes information concerning a particular antibiotic disk of the plate. For example, the information may include disk size, disk shape, disk location, antibiotic name, concentration, etc.

Figure 9:
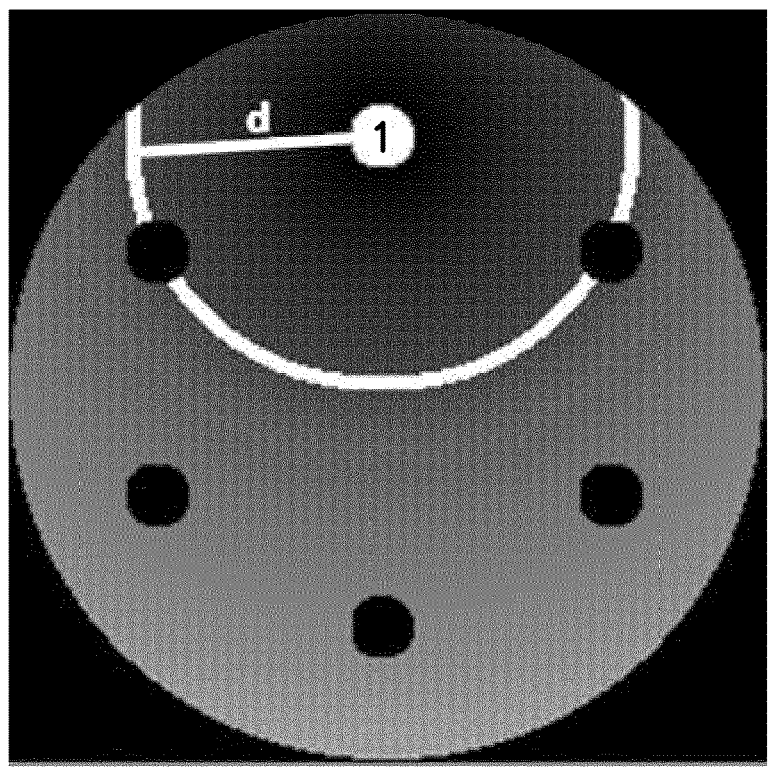
FIG. 9 is an image representation of the graph of FIG. 8, for a single disk of a plate, masking out image information associated with the other disks of the plate and the area of the image outside of the boundary of the plate.

For each disk, the process may optionally evaluate the growth level modulation as a function of distance to the edge(s) of the antibiotic disk. For example, contrast information on a pixel by pixel basis, serving as pixel characteristic data, may be derived for the pixels of the second image of the plate relative to the first image of the plate. This characteristic data may include any one or more of intensity value, color value(s), grey value, opacity value and blurring value for each pixel of the evaluated image. Optionally, these values may also be characterized according to their distance from a particular disk. Such a distance is illustrated in FIG. 9. For example, the pixels may be summarized as a function of distance, such as in a distance map.

Figure 5:
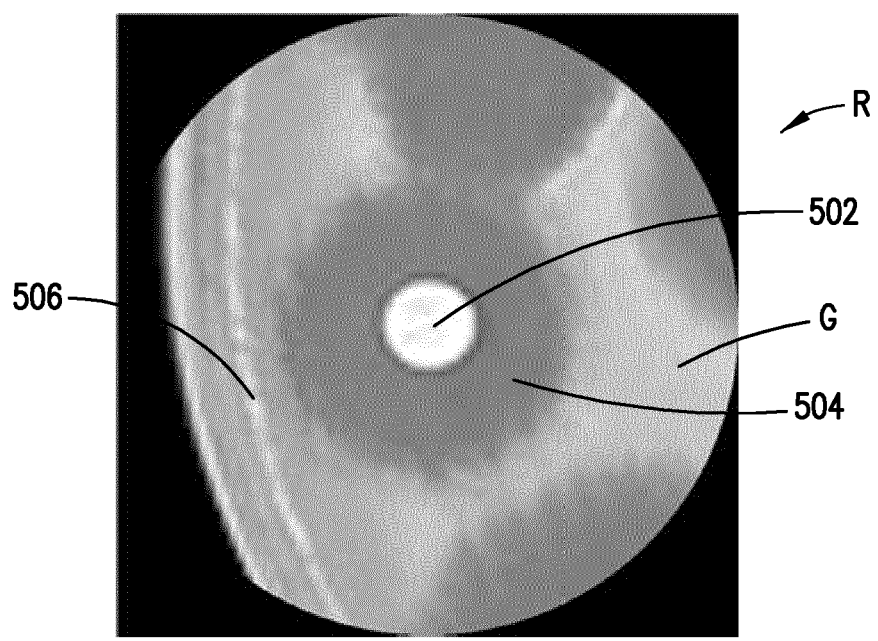
FIG. 5 is an image of a minimum inhibitory zone about an antibiotic disk of a growth plate after incubation and/or significant growth time where bacterial growth has occurred.
Figure 6:
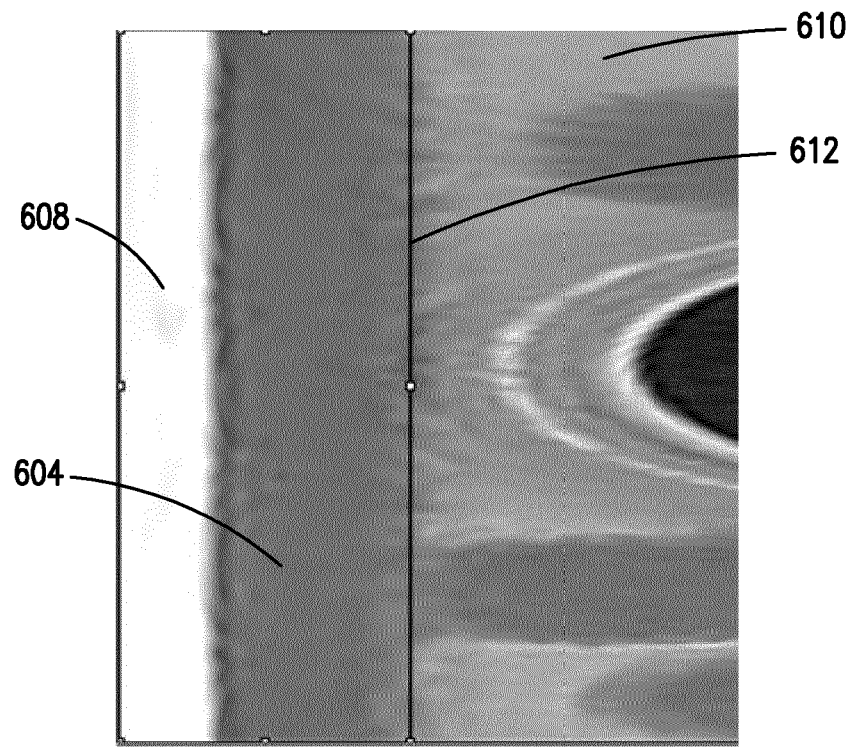
FIG. 6 is a converted version of the image of FIG. 5 where the images has been converted by a polar transform, illustrating a minimum inhibitory distance from the disk.
Figure 7A:
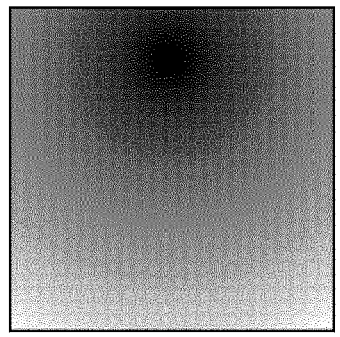
FIGS. 7A to 7F are greyscale images illustrating a mapping of intensity values for the pixels of each disk of FIG. 7 as a function of radial distance from each disk; where shading represents distance from the disk with intensity becoming lighter with increased distance from the disk.
Figure 7F:
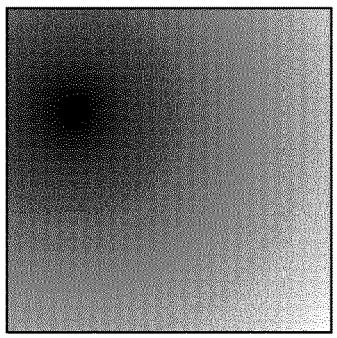
Figure 7B:
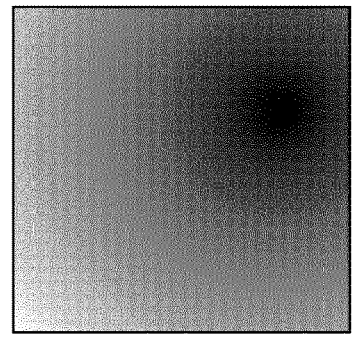
Figure 7:
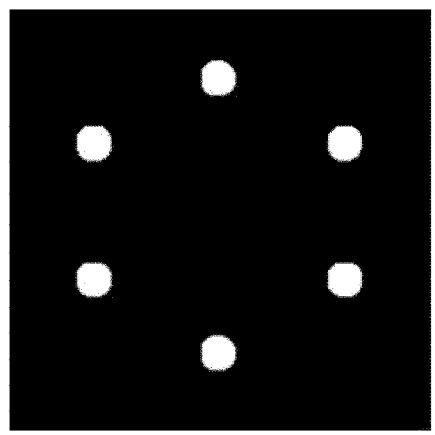
FIG. 7 is an image of a plurality of antibiotic disks on a plate.
Figure 7E:
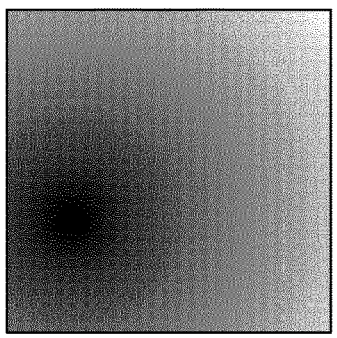
Figure 7C:
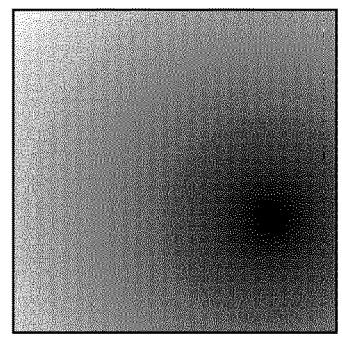
Figure 7D:
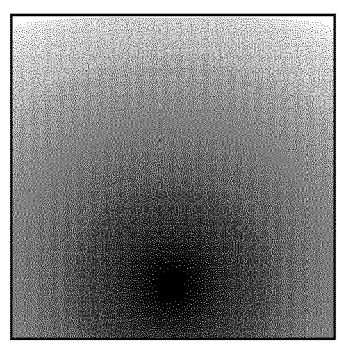

An example of such pixel characteristic data may be considered in reference to FIG. 5 and FIG. 6. FIG. 5 includes a portion of an image of an AST growth plate showing a region R with one antibiotic disk 502. A no-growth region 504 exists around the disk 502. Growth regions G exist further away from the no-growth region and disk 502. The image also shows the plate edge 506. FIG. 6 shows a polar transform of contrast information that may be derived from a comparison of the image of FIG. 5 and the corresponding region from an earlier image (not shown). In FIG. 6, pixels are displayed as intensity values. The polar transformation converts the disk 502 portion of the image of FIG. 5 into a light band 608 (highest intensity) at the left of the image. In the transformation, the no-growth region 504 is converted to no-growth band 604 having a lower intensity than the light band 608. A growth region 610 showing growth G having a higher intensity than the no-growth band 604 and lower intensity than the light band 608. Edge detection may optionally be employed to detect an edge 612 between the pixels of light band and the no-growth band and/or to detect an edge between the pixels of the no-growth band and the pixels of the growth region. As illustrated in the image of FIG. 6, edge detection can determine an edge between the pixels of the no-growth band 604 and the pixels of the growth region so as to indicate or determine the minimum inhibitory distance for the particular antibiotic disk 502 and the bacteria growth on the plate.

Figure 8:
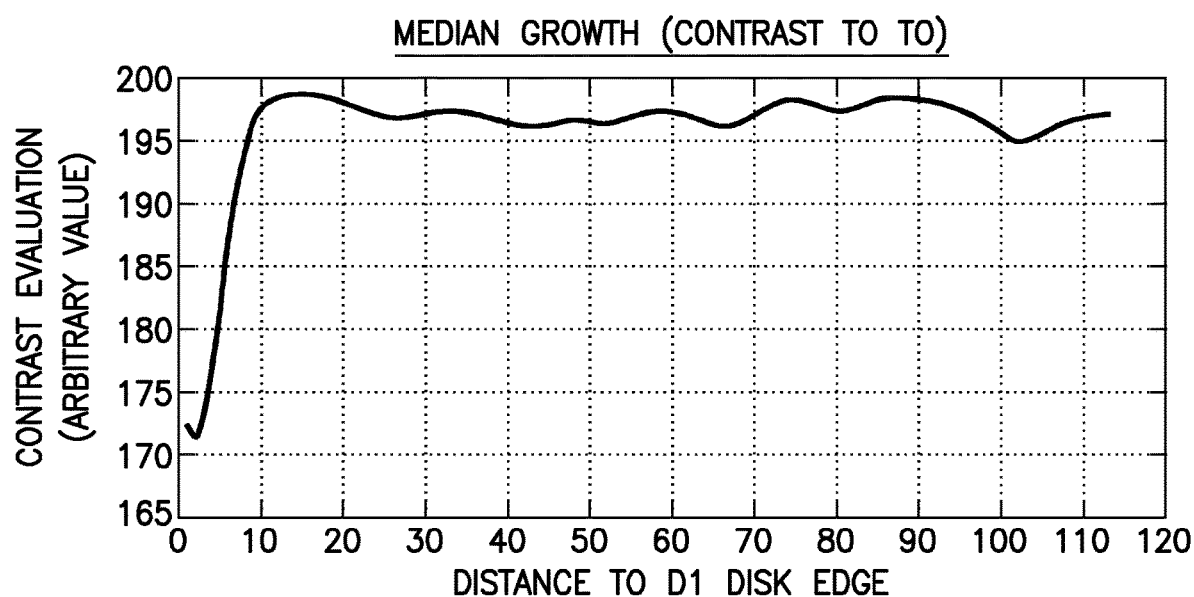
FIG. 8 is a graph mapping growth (e.g., contrast) as a function of radial distance from the antibacterial disk D1 of FIG. 4 determined according to median pixel values (e.g., one or more of intensity, opacity, color, blurring, etc.).

With the polar transformation of the pixels of the image, intensity values may be summarized as a function of distance from the disk such as to form a distance map. (See, e.g., FIG. 8.) For example, each column ($x_c$) of n pixels ($x_c$, $y_{0\ldots n}$) may be averaged where $x_c$ represents a fixed pixel distance from the disk center or disk edge. The average for each distance $x_c$ may then collectively provide the distance map. Other distance maps may similarly be formed such as by finding the maximum, minimum, average, median and/or any percentile value of the pixels for each column. In addition to these intensity distance maps, other such maps may be formed with color value(s), grey values, opacity values and blurring values associated with the pixels of the image. Although the polar transform can be utilized to facilitate pixel characterization according to distance as described herein, in some versions polar coordinates may be utilized to characterize pixels according to distance from the disk without transformation of the contrast data. Polar transformations of the image pixels are described in further detail below.

In some versions, the map(s) that summarize the plate may then be used for further evaluation of the particular AST plate undergoing testing. However, the maps may also, or alternatively, be stored in a database in association with information concerning the particular antibiotic disk(s) (e.g., type, concentration, etc.) of the plate and information concerning the particular bacterium tested so that the maps may be used for modeling as discussed in more detail herein.

Continuing with the process of FIG. 2 for an evaluation of the particular AST plate image, the system may access growth model data concerning any subset of, or all of, the disks of the AST plate being tested. Such access may involve selecting data from a memory, such as a database, of the data storage medium 130. Access to the memory may be based on the recognition of the marking of the disks of the AST plate as previously described and/or based on a plate marking that is associated with the particular AST plate and its contents. In some versions, the access may retrieve data from the database(s) where the data includes, for example, one or more distance maps, antibiotic concentration data, growth model functions, etc. that concern one or more of the disks of the AST plate and, optionally, a bacterium being tested. The growth model data, including such maps or functions, may be derived according to a growth model as described in more detail herein and may be further based on observed image data, such as map functions from other AST plates. Typically, each disk may have a particular distance map or a set of distance maps associated with the disk. Thus, the distance maps may vary depending on the particular antibiotic, the concentration of the antibiotic on the disk, the amount of time lapsed from placement of the antibiotic on the disk. Optionally, the distance map for a particular antibiotic disk may also be dependent on the type and concentration of neighboring antibiotic disk(s) of an AST plate.

Figure 10:
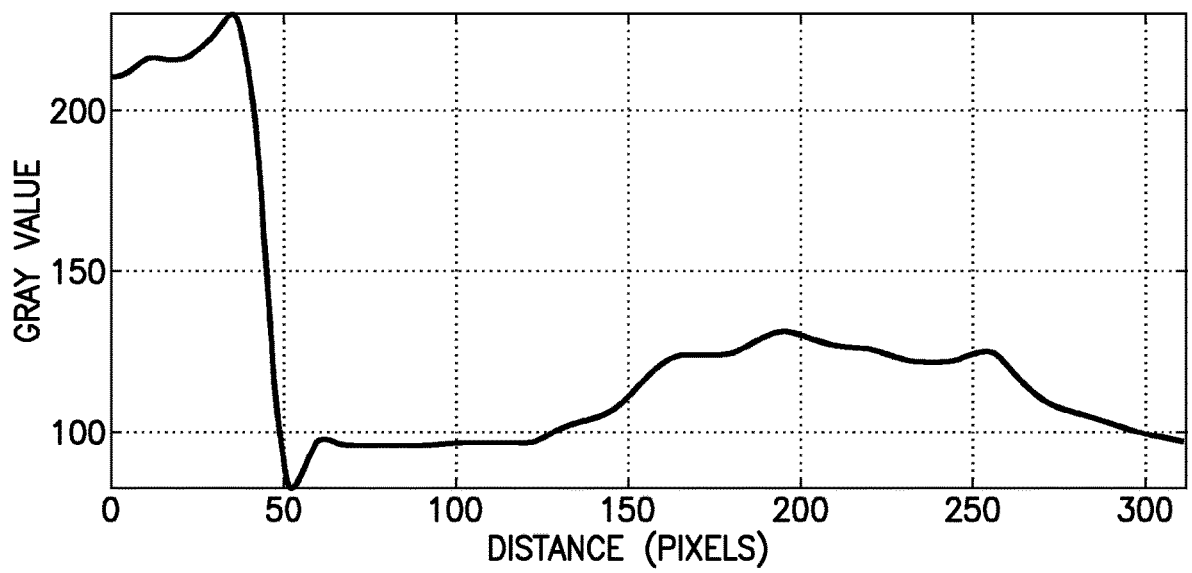
FIG. 10 is a graph illustrating a growth model function according to a growth model that maps pixel gray value according to radial distance from a model antibacterial disk for a modeled bacterium.
Figure 11:
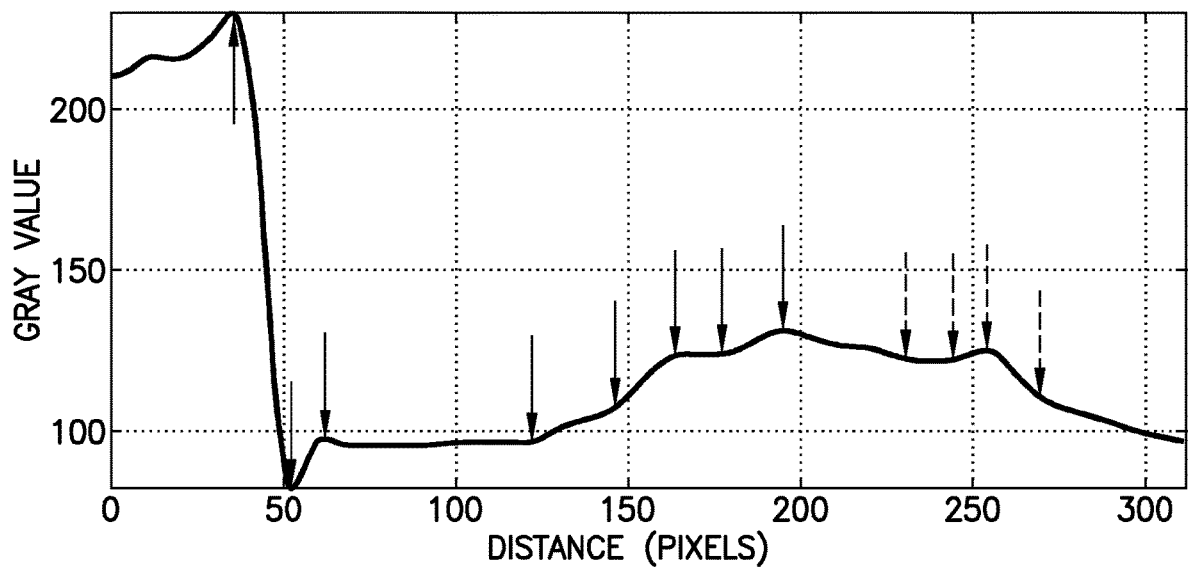
FIG. 11 is the graph of FIG. 10 showing characteristic points of the model at various distances.

Example distance maps that are derived by a growth model may be considered in reference to the example map of FIGS. 10 and 11. In the example of FIG. 10, the distance map, similar to the previously described maps, provides an estimation of a radial profile that is indicative of bacteria growth as a function of distance from a center of a particular disk. For this particular map, changes in gray value are associated with distances (e.g., pixel distance) from the edge of an antibiotic disk. For example, higher gray values may be an indication of modeling an absence of growth and lower gray values may be an indication of modeling bacterial growth. In this example, the gray values of the function may be considered an average gray value. However, other functions may employ minimum values, maximum values, median values and/or percentile values. As illustrated in FIG. 11, the function may have characteristic points (illustrated with arrows) that may be indicative of different features of the relationship between the bacteria and the particular concentration of the antibiotic from the disk (and potentially neighboring disks) with respect to the distance from the antibiotic disk. For example, points in the illustrated function indicate features such as the edge of the antibiotic disk, the maximum effect on growth (i.e. the maximum amount of growth modulation and its distance from the disk), the distance from the disk at which 50% modulation of the growth response occurs, etc.

In some versions, these model maps may be compared to the observed maps made for the particular AST plate in process 216 to detect and indicate differences between the model distance map and the observed distance map. Such a comparison process may involve discrepant analysis. In some such versions, the comparison may involve generation of a simulated image according to a model map. Thus, at process 220, the system may generate the simulated image data with a growth model function using growth modeling data that was accessed at 218. The simulated image data thereby simulates growth (and/or no growth) on the AST growth plate in relation to one or more disks of the plate.

For image maps (either for the image under test or for images in the library of images of plates with different patterns of microbial growth modulation for specific microorganisms, antibiotic and antibiotic concentration), growth can be simulated as a modulation of observable growth when there is no AB disk (or an infinite distance to AB disk). For example, $C_{no\ AB}$ is the measured contrast developed by the growing organism after incubation time t when there is no AB disk (i.e. this is the same as growth that occurs at an infinite distance from any antibiotic disk (a zone of absolutely no inhibition by the disk)).

Figure 16:
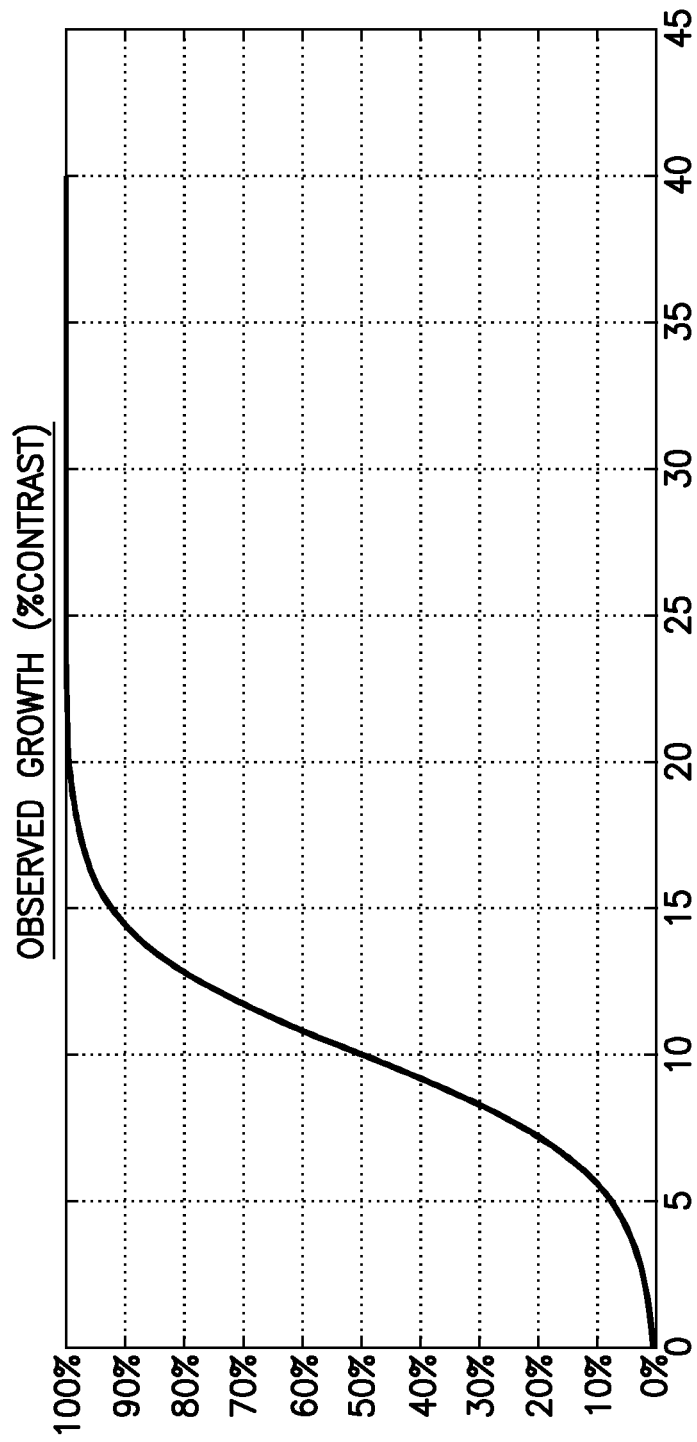
FIG. 16 illustrates a model of growth that occurs when a disk carries antibiotic where growth is strongly modulated within 10 mm of the disk and where the growth response to the antibiotic disk is modeled as a function of growth modulation in relation to distance from the edge of the disk.

The observed contrast can be modeled using the following sigmoid function:

$$f_{\lambda(x)=C(x)} = \frac{C_{no\ AB}}{1+e^{-\lambda(x-r)}}$$

with r equal to the distance from the disk showing a 50% modulation of observed contrast and x equal to the distance to the AB disk edge for the particular pixel. The value is zero if no such modulation of microbial growth is found (as evidenced by a lack of contrast difference between the pixel and pixels in a region of unmodulated microbial growth). compared to regions far away from the antibiotic disks. In case of modulation, the value $\lambda$ is a factor controlling the steepness of the modulation near the disk (the slope equals $\lambda/4$ in r). Referring to FIG. 16, when the measured temporal contrast due to growth is equal to 100% (i.e. $C_{no\ AB}$), r is equal to 10 mm and $\lambda$ is equal to 0.5 (where larger values give steeper slope), the maximum contrast is seen about 20 mm from the disk edge and remains constant (i.e. no negative modulation of growth further away from the AB disk) and the maximum slope is seen at R equal to 10 mm. Compare FIG. 16 with FIG. 8 and the same function is observed.

The following can be used to optimize for the match between measured and simulated contrast:

$$\int_{x=0\ mm}^{x=40\ mm}(C_M(x)-C_S(x))^2$$

Where $C_M$ is the measured contrast and $C_S$ is the simulated contrast. The modeled growth can be adjusted by first setting $C_{no\ AB}$ and then searching for the distance r (in the range 0 mm to 45 mm) where modulation of growth is 50%, using a value of $\lambda$ equal to 10. The value of $\lambda$ in the range of 0.1 to 10 is refined or the slope in r is estimated to set the value of $\lambda$. According to the function, the slope at the value r is $\lambda/4$.

Figure 13:
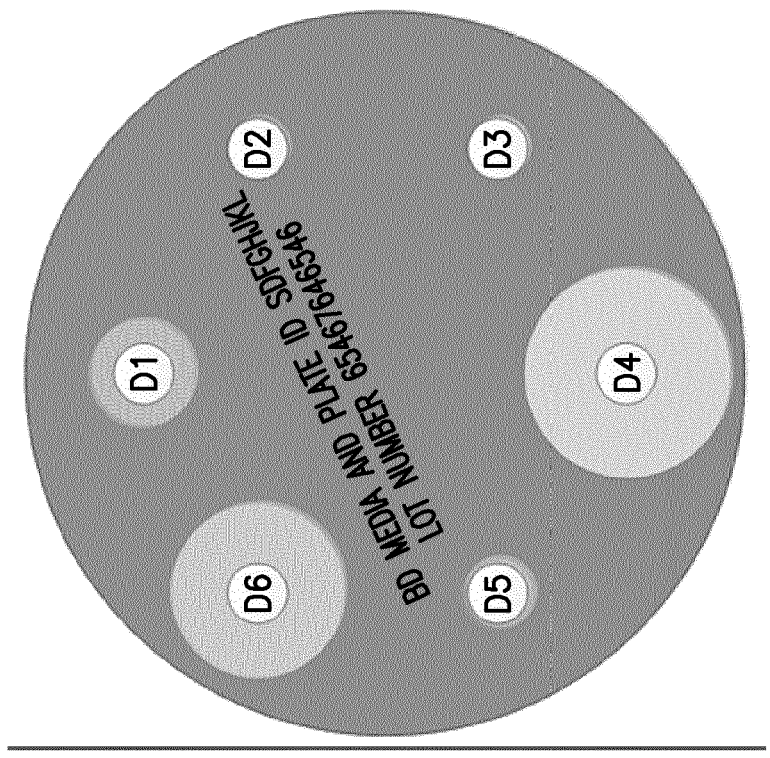
FIG. 13 is a simulated image generated according to a growth model function (e.g., one or more for each disk) where interaction occurs between some of the modeled antibiotic disks and the modeled bacteria.
Figure 12:
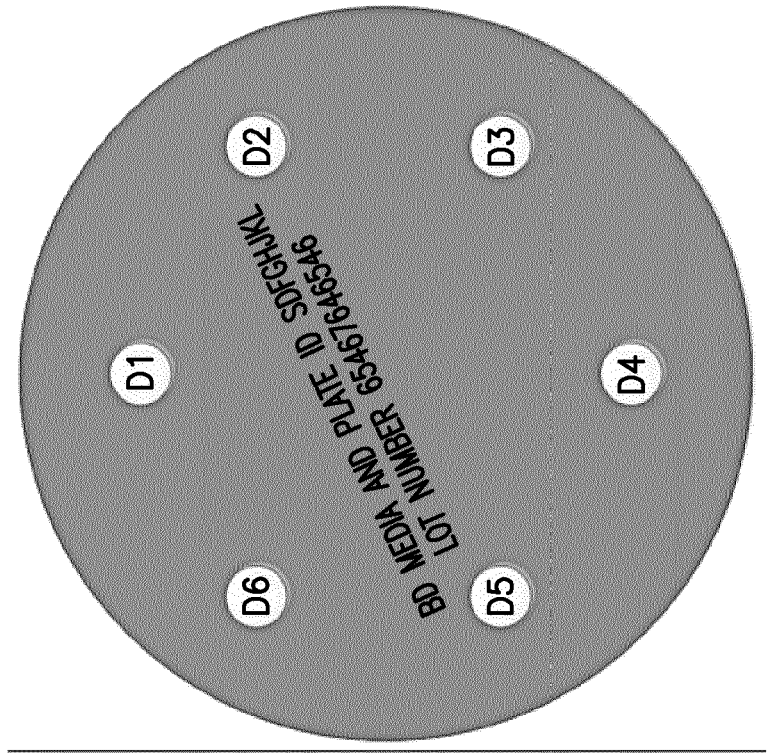
FIG. 12 is a simulated image generated according to growth model function(s) (e.g., one (intensity) or more (color, opacity, blurring) for each disk) where no interaction occurs between the modeled antibiotic disks and the modeled bacteria.

For example, as illustrated in FIG. 12, an AST plate image may be generated from a set (one or more) of model distance functions where the modeled distance functions have modeled growth. Such functions may include opacity value functions, color functions and blurring functions that each apply a particular value from the map to each pixel of the simulated image according to its distance from a disk and the map function(s). In the example of FIG. 12, growth is shown even around the disks because the model functions (not shown) modeled growth for the particular disks and the particular bacteria of the plate such that the bacteria were unaffected by, or resistant to, the antibiotic of the disks (i.e., no area of inhibition). FIG. 13 in contrast thereto, shows a simulated image with inhibition areas in some areas because the model functions for the particular disks model the different inhibitory effect of the antibiotic(s) and/or their concentrations.

Many examples of images of growth modulation/inhibition adjacent antibiotic disks are found at http://cdstestmet/manual/plates/. Such images are provided for purposes of illustration in FIGS. 17-20 and FIG. 21A-F. As can be observed in FIG. 17, dark rings around antibiotic disks are zones of inhibition. Hazy regions indicate diffuse growth. Lighter regions at the perimeter such as those illustrated in Plate 13.2.0 for the disk VA5 indicated reduced inhibitory zones (i.e. partial modulation as opposed to complete modulation). When the background extends to the perimeter of the disk, as in plate 13.2 D for disks VA5 and TEC15, this image shows that growth was not modulated/inhibited for this microorganism (*Leuconostoc*) for those antibiotic disks (at those concentrations).

Figure 18:
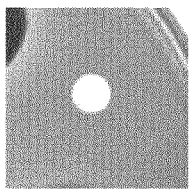
FIG. 18 illustrates microbial growth on a culture dish carrying an antibiotic disk where the disk causes no growth modulation (i.e. no inhibition).
Figure 19:
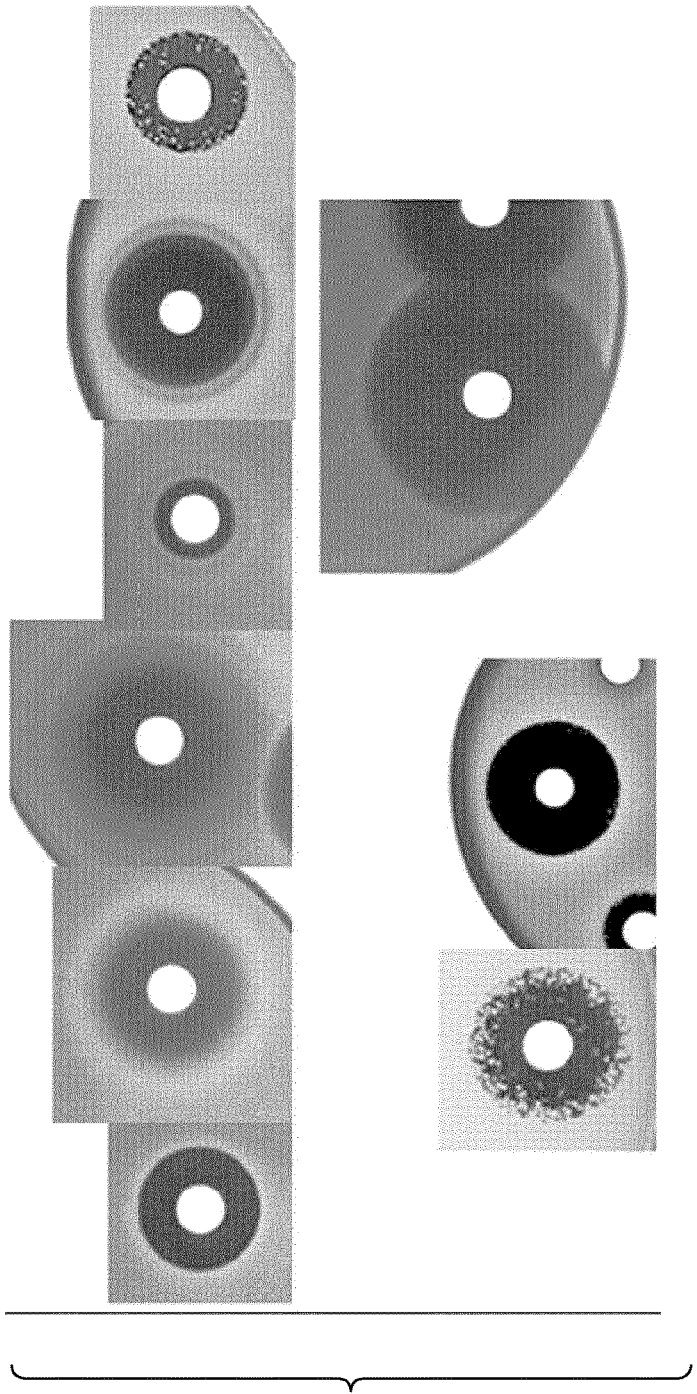
FIG. 19 illustrates a variety of microbial growth modulation for different microorganisms caused by different antibiotic disks.

There are three distinctly different scenarios for modeling growth. The first scenario is where the growth is simply not modulated by the antibiotic disk. This pattern (i.e. lack of modulation) is illustrated in FIG. 18. Where growth is modulated by a single disk the modulated/inhibited growth will manifest in a wide variety of patterns (depending on the specific microorganism and the specific antibiotic). A series of non-limiting examples of such growth modulation is illustrated in FIG. 19.

Figure 20:
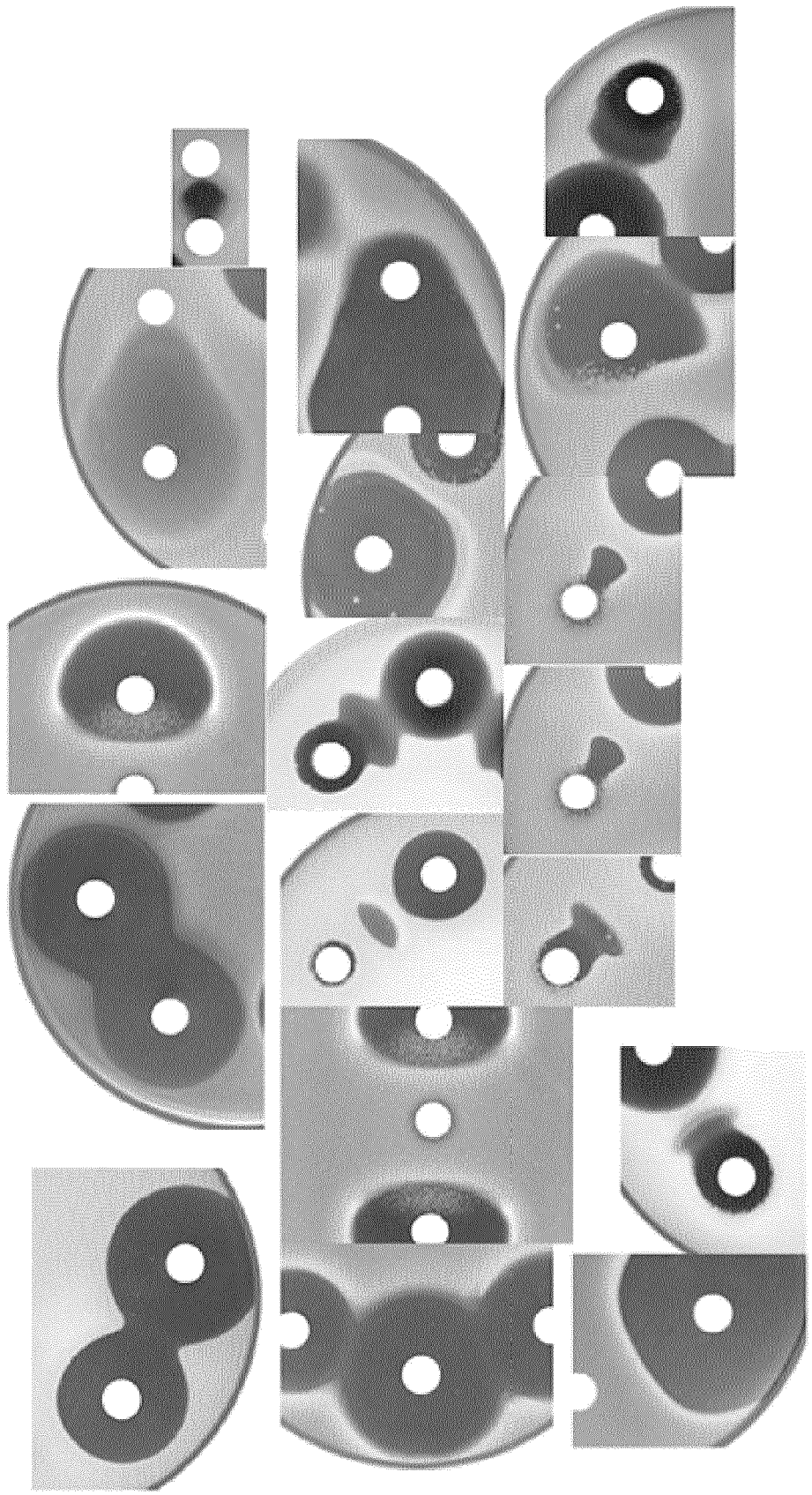
FIG. 20 illustrates microbial growth modulation influenced by adjacent disks.

Growth modulation influenced by multiple antibiotic disks can also assume a variety of patterns which vary depending upon microorganism type, the antibiotics and the distance from the multiple disks. Such patterns are illustrated in FIG. 20. As noted above, a wide array growth modulation patterns can result depending upon a variety of factors (i.e. the microorganism, the antibiotic carried by the disk, the concentration of the antibiotic on the disk, the proximity of disks to each other on the plate, etc.). Models that will simulate the modulation of microbial growth for a microorganism by a selected antibiotic to interpret image data therefore vary in complexity depending upon the interactions being modeled.

Figure 21B:
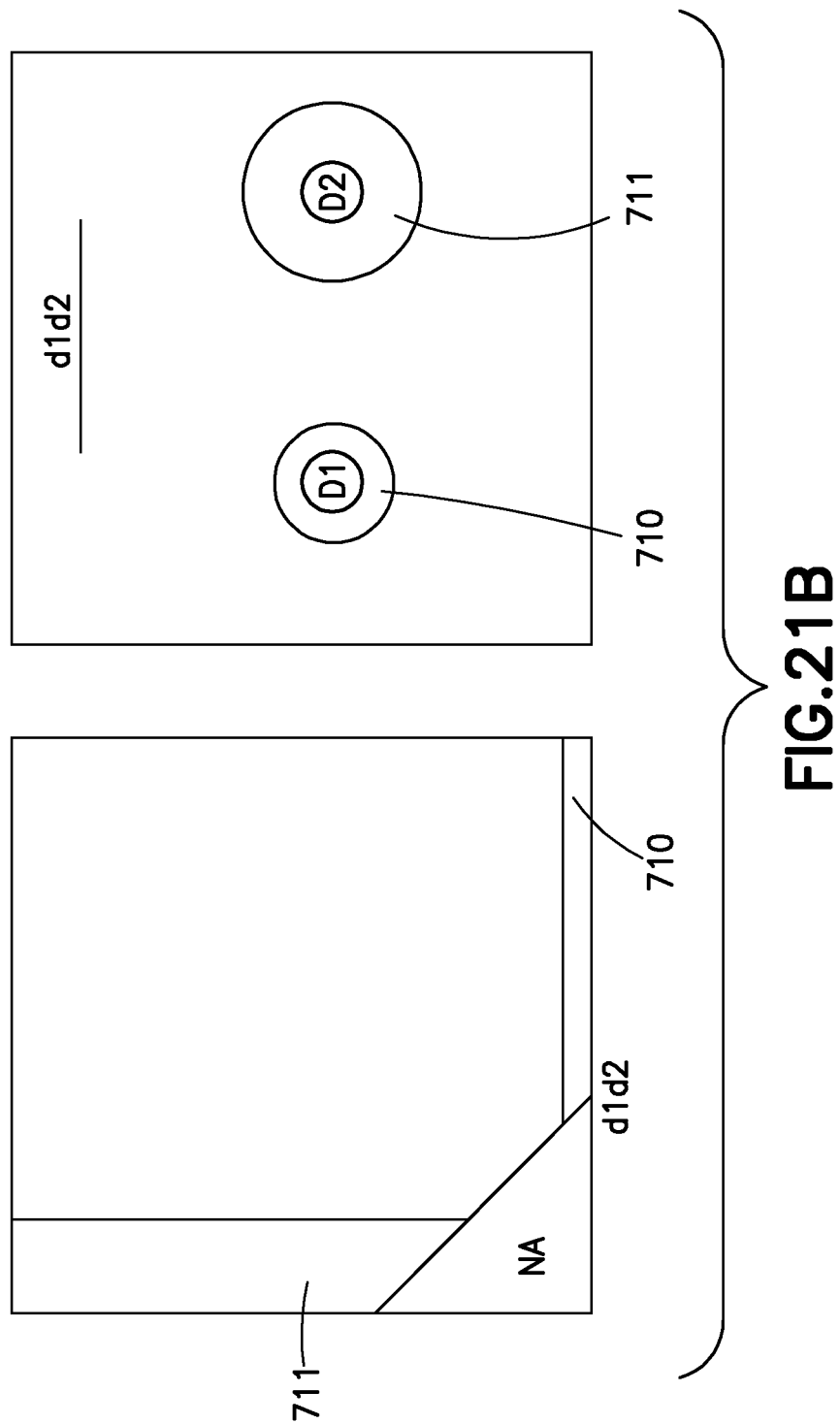

In order to evaluate areas on a plate where microbial growth is modulated by multiple disks, it is useful to transform intensity of the pixels as function of distance from the two disks. Referring to FIG. 21A, an illustration of the modulation caused by disk D1 is illustrated as a light ring around the disk. No modulation is caused by disk D2. On the left, the transform of the image is illustrated. The distance from disk D2 is on the x axis and the distance from disk D1 is on the y axis. The intensity of the pixels in the zone of modulation (700) is illustrated as 700 in the two-dimensional transform. There is a zone in the transform that does not represent a distance combination from the two disks, which is what is illustrated by 701. A two-dimensional transform where two disks each cause modulation (i.e. a disk does not influence the modulation caused by the other disk) is illustrated in FIG. 21B. The zones of modulation (710, 711) are illustrated relative to disks D1 and D2 on the right and in the two-dimensional transform on the left.

A more complex interaction is illustrated in FIG. 21C. There are modulation zones 720 and 721 as in the prior examples. However, there is clearly a zone where modulation caused by the disks overlaps. The overlap in influence is apparent in the transform on the left because the zones of modulation extend into each other.

Figure 21D:
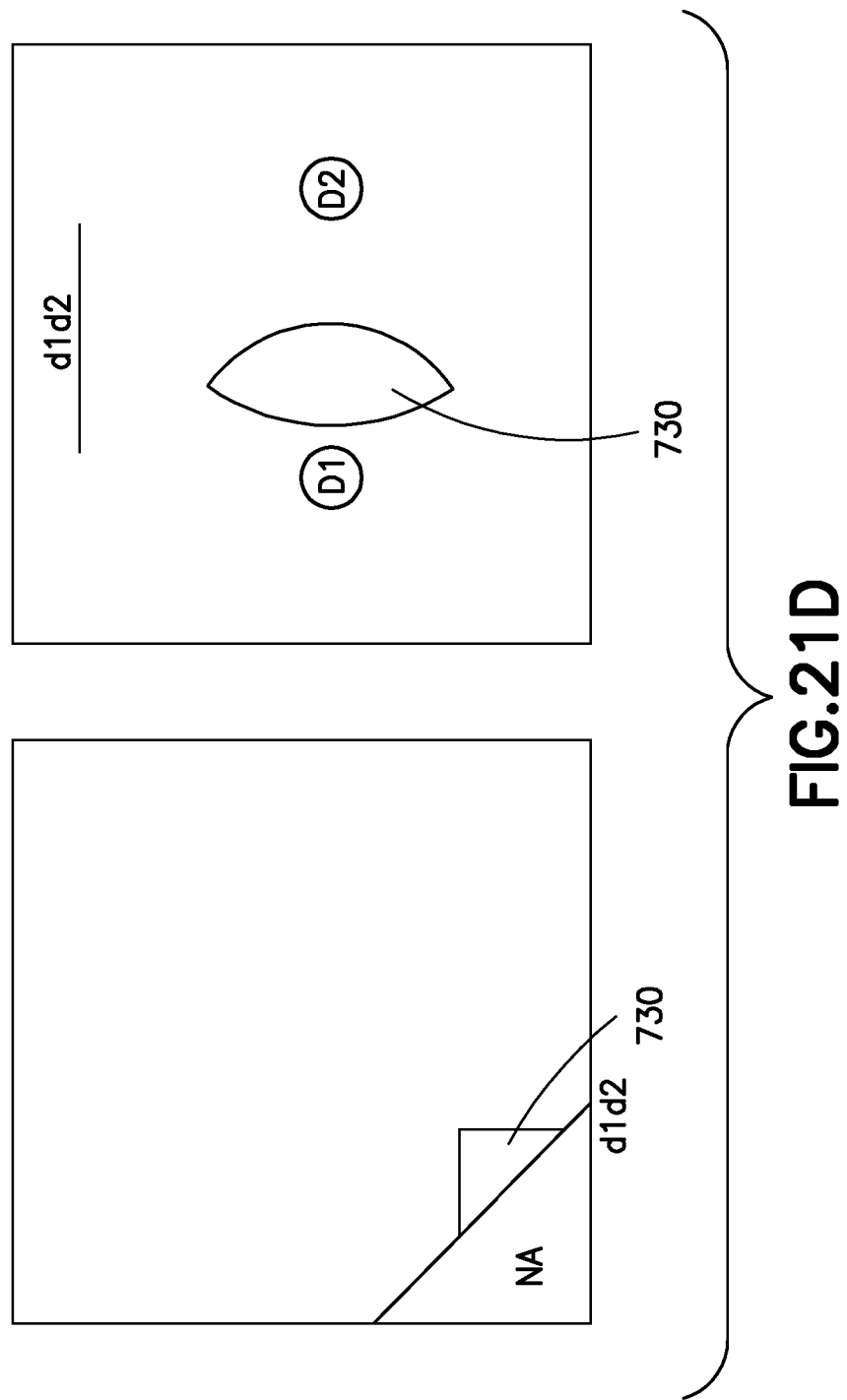

Referring to FIG. 21D, there illustrates a situation where, individually, the disks cause no growth modulation. However, some distance from both disks, a zone of modulation 730 is present, indicating that the growth modulation is caused by the combination of the two antibiotics and not by each disk individually. By transforming the image data in this matter, patterns for certain combinatorial effects of multiple disks are more readily compared with existing patterns to interpret the image data from the plate under inspection.

Figure 21E:
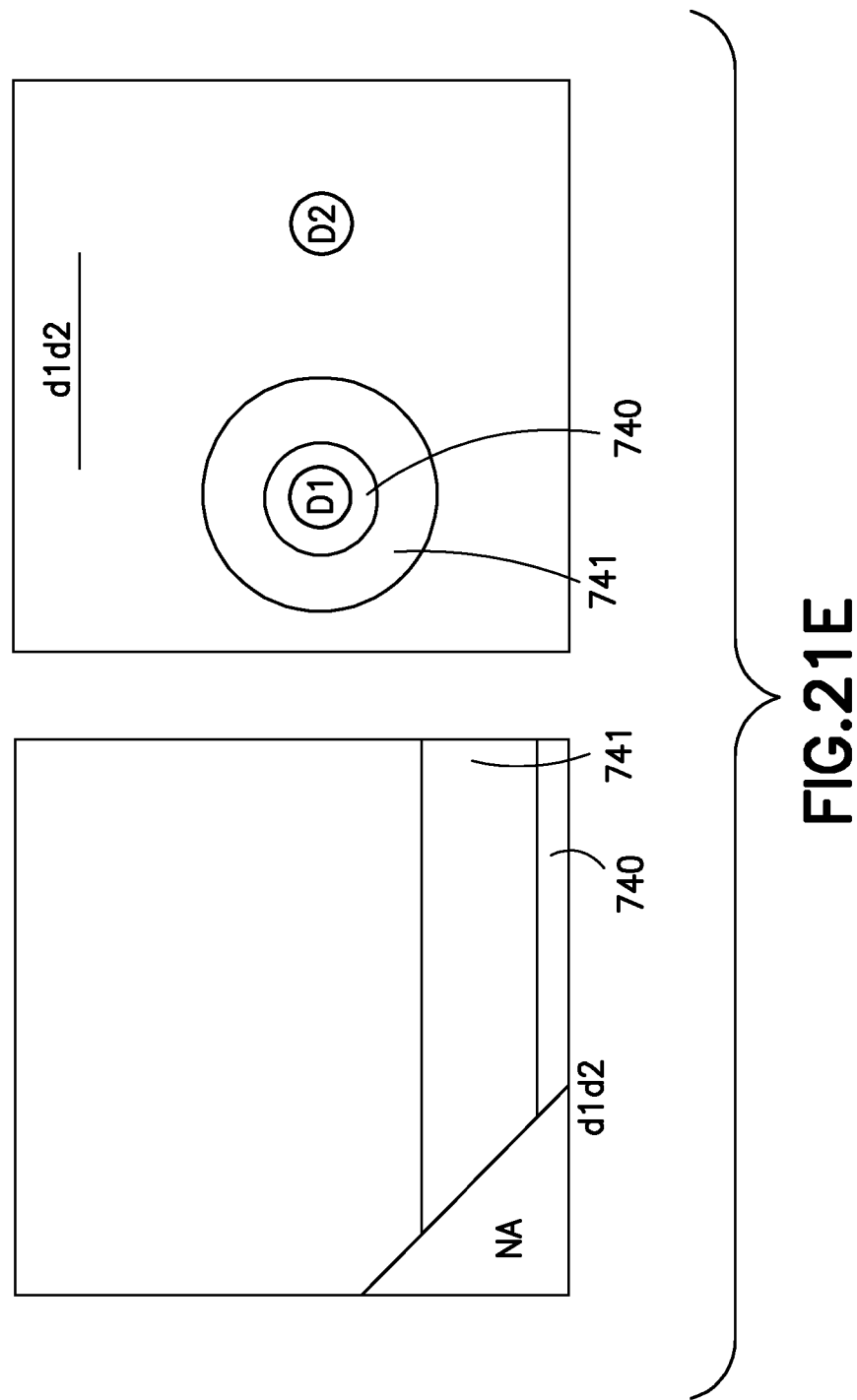

In some instances, the degree or extent of modulation can vary with distance from the disk. FIG. 21E illustrates first (740) and second (741) zones of modulation caused by disk D1. The first zone is 740 complete inhibition and the second is a zone of partial inhibition. Since pixel intensity will vary as function of the extent of modulation, the differences in intensity are also apparent from the transform data on the left. For simplicity of illustration, no modulation is caused by D2 in FIG. 21E.

Figure 21F:
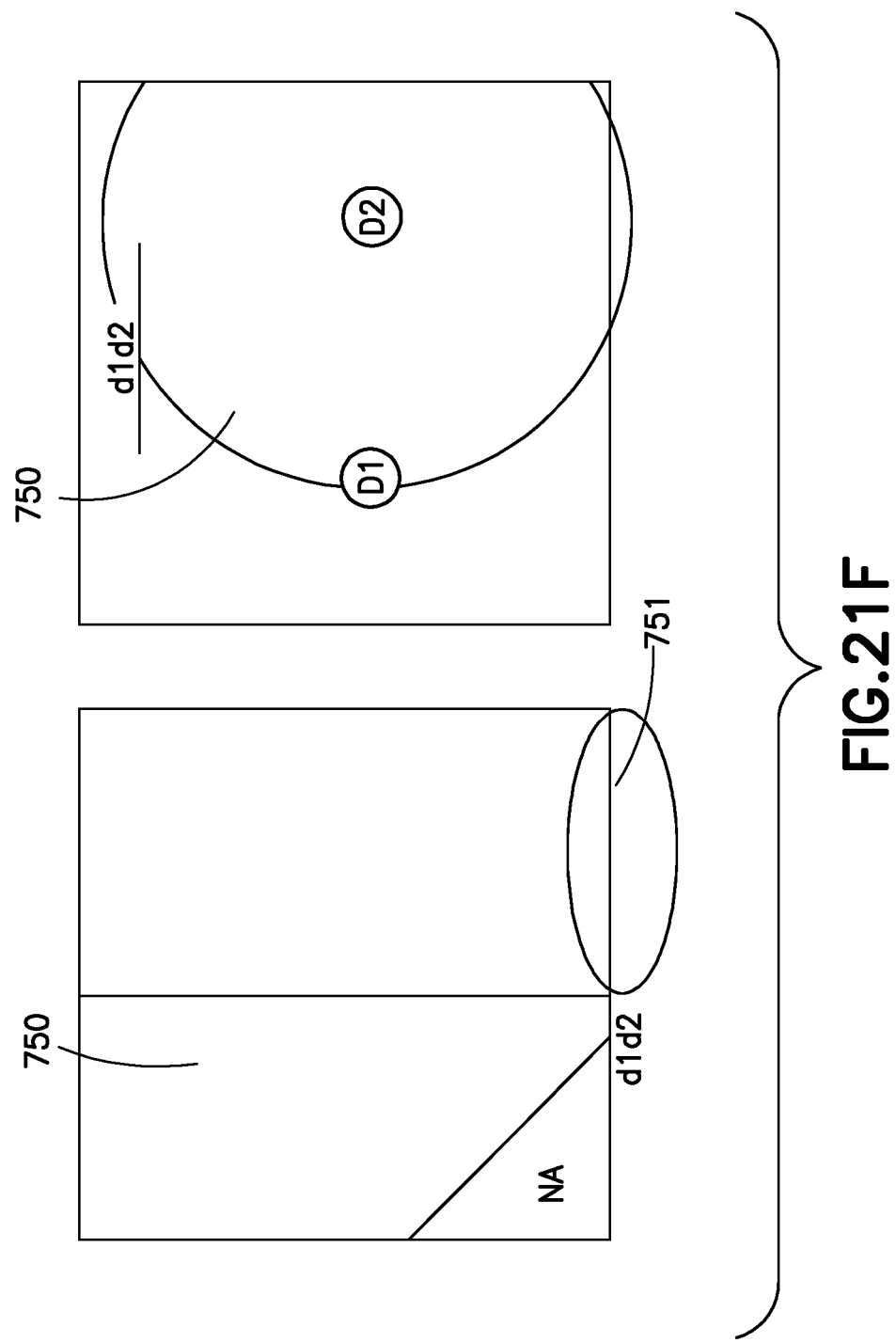

FIG. 21F illustrates a transform where the modulation 750 caused by D2 swamps D1, which causes no modulation itself. While this might be difficult to discern from a three-dimensional image, it is clear from the polar transform data that pixels directly adjacent to D1 (illustrated as region 751 in the transform data) have an intensity consistent with no modulation (i.e. the distance d1 from D1 is zero for many pixels that possess an intensity consistent with zero growth modulation).

Figure 15:
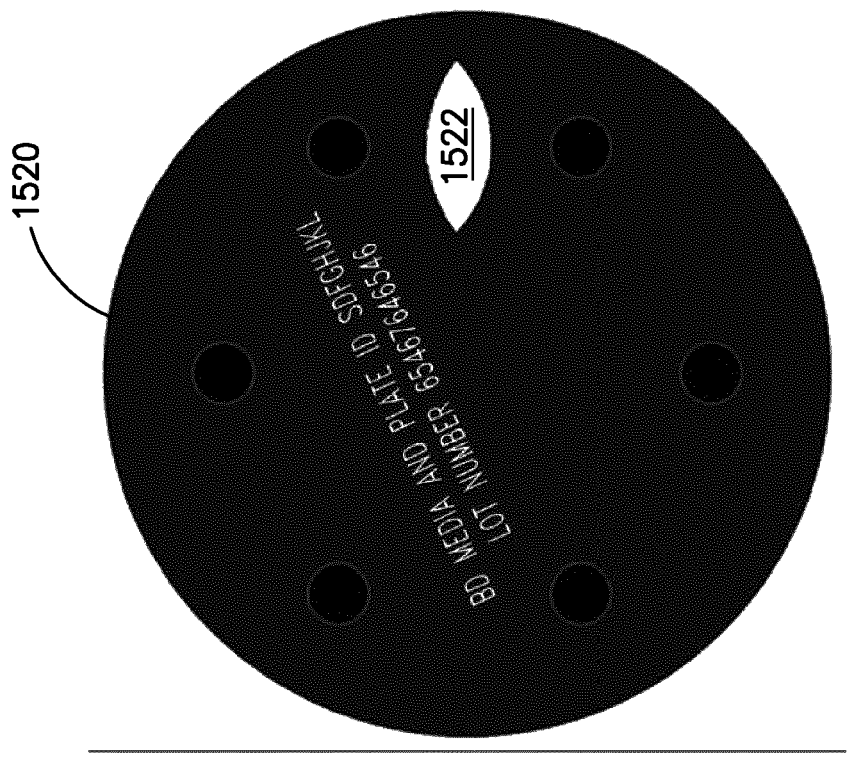
FIG. 15 represents a comparison of the pixel characteristic information and the simulated image that identifies pixel regions (such as in an image mask) for further evaluation and/or analysis.
Figure 14:
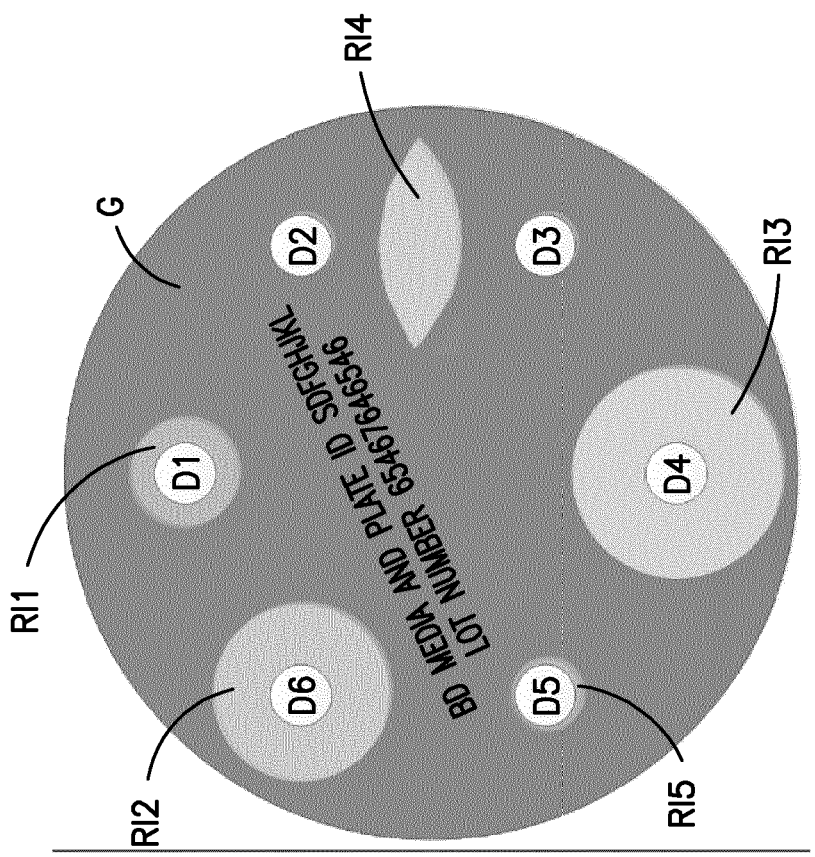
FIG. 14 represents pixel characteristic information for an observed image derived from an image sensor such as by contrast analysis that compares multiple images (e.g., before and after a growth time).

Such simulated images may be applied by the system 100 to make susceptibility testing more efficient. For example, at process 222, the system may compare the simulated image generated by the system to an image of the AST plate that is captured by the system. Such a comparison may serve to contrast the captured image and the simulated image by discrepant analysis. For example, FIG. 14 illustrates an image (or contrast image) captured by the system such that it shows growth G and various regions of inhibition (RI1, RI2, RI3, RI4 and RI5) about some of the disks. Such an image, which may be referred to an observed image, may be processed in relation to an earlier image to enhance the contrast indicative of a growth observation as previously discussed. This observed image may then be contrasted with the simulated image. For example, as illustrated in FIG. 15, an image mask 1520 may be generated to highlight areas of difference between the observed image (FIG. 14) and the simulated image (FIG. 13) so as to highlight differences between the modeled growth and the observed growth. For example, the image mask may be generated by a comparison of pixels, on a pixel by pixel basis. In such an example, if a given pixel (x,y) of the observed image has a value the same as, or not significantly different (e.g., within a difference threshold) from the corresponding pixel of the simulated image, the corresponding pixel of the image mask may be set to a desired value (e.g., black). Otherwise, the corresponding pixel of the image mask may be set to a different value (e.g., white) to highlight the location of the difference. In some cases, the mask image may be generated with pixels according to a scaling of the differences such that regions of greater differences stand out more from regions of lesser differences.

Such discrepant analyses of the model versus the observed images can serve as a basis for confirming the model. It can serve to identify/highlight regions not well explained by the model. It can also help to simplify automated detection of antibiotic disk interactions and further analysis. In this regard, as illustrated with respect to FIGS. 13, 14 and 15, disks D1, D4 an D6 have expected antibiotic effects (i.e., modeled FIG. 13 approximately equal to observed FIG. 14) having typical regions of inhibition. However, a partial region of inhibition RI4 between disk D3 and D2 seen in FIG. 14 indicates some unexpected interaction between the antibiotic of D2 and the antibiotic of D3. This results in a difference region 1522 being presented in the mask of FIG. 15. Such a difference image or mask can serve as a tool to assist with a visual assessment of the AST plate, such as if it is presented on a display to a lab technician, either with (e.g., near) the observed image or overlaid with the observed image. Also, such an assessment can serve as a basis to compare with a library of simulated or image data. Such comparison can yield a plate assessment without requiring operator intervention to assist in the interpretation. Thus, the system 100 may be configured with a display (e.g., monitor screen) to present such imaging on the display along with an assessment of the meaning of the image (if the system is able to provide such assessment). In this way, a particular synergy between two different antibiotics may be detected by the data of the difference image.

The processes of the system 100 described herein can also permit incrementally modeling of the AST response. For example, by adjusting the model after each step with the detected difference between the model and the observation, the next level in the model may be modified for further detections. Any final discrepancy between the model and the true image can highlight model inadequacy for automatically interpreting the AST. Thus, the system can learn so as to improve or update the model for automated detection.

The system can improve automatic detection of any of:
growth characteristics (where there is no growth modulation induced by one or more antibiotics)
fine interpretation of growth modulation as induced by a given antibiotic
microbial population heterogeneity in case of different susceptible/resistant subpopulations or mixed organism
complex resistant/susceptible patterns due to synergy of two or more antibiotics.

Growth Modeling Theory Development

In some versions of the present technology growth modeling data, such as the distance maps previously discussed, which may be understood to be calibration diffusion maps, may be based on antibiotic concentration, testing/diffusion time, and selected bacteria. In developing such maps for a growth model, growth modulation may be measured as a function of "sensed" concentration (a location at the edge of bacteria growth and no growth) depending on pixel location on agar plate as a function of distance to each and every disk.

The "sensed" concentration for each antibiotic should follow the following equation:

$$C(r, t) = C_0 \frac{1}{\left(\sqrt{4\pi Dt}\right)^k} e^{-\frac{r^k}{4Dt}}$$

Where:
$C_0$ Is the initial concentration of the disk, D is the diffusion coefficient (Stokes-Einstein equation), t is the time, r the distance to source (to the edge of the antibiotic disk); k=dimensionality (typically between 1.0 and 3.0), most often close to 2.0.

Concerning the calibration diffusion maps for each antibiotic, disks with different loads of a given antibiotic may be used and the respective growth patterns may be analyzed for a given susceptible organism. De facto, the limit of each inhibition zone should correspond to the same "sensed" concentration of antibiotic by the organism. Thus, with a set of inhibition zone radii and known antibiotic load, the diffusion equation may be solved for each antibiotic.

Based upon antibiotic critical concentrations and critical diameters, r, at reading time (e.g., t=24 h), D and k can be estimated.

For example, using two disks with initial concentration $C_1$ and $C_2$ and inhibition radii r1 and r2 this gives:

$$C_1 \frac{1}{\left(\sqrt{4\pi Dt}\right)^k} e^{-\frac{r_1^k}{4Dt}} = C_2 \frac{1}{\left(\sqrt{4\pi Dt}\right)^k} e^{-\frac{r_2^k}{4Dt}}$$

$$\text{Or } \ln\left(\frac{C_1}{C_2}\right) = \frac{r_1^k - r_2^k}{4Dt}$$

If C1, C2, C3 . . . are two-fold cascade dilutions with C2=½ $C_1$, C3=½ $C_2$ . . . then:

$$\ln(2) = \frac{r_1^k - r_2^k}{4Dt} = \frac{r_2^k - r_3^k}{4Dt}$$

Or $r_1^k - 2r_2^k + r_3^k = 0$ from which k can be easily estimated.

The finalization of the calibration can be brought into the equation calibration if the minimum inhibition concentration ("MIC"), or C (r, t), of the tested organism is provided in parallel using an automated testing system to refine the calibration equation.

$$C(r, t) = C_0 \frac{1}{\left(\sqrt{4\pi Dt}\right)^k} e^{-\frac{r^k}{4Dt}}$$

Let B be 4Dt. then:

$$MIC = C_0 \frac{1}{\left(\sqrt{\pi B}\right)^k} e^{-\frac{r^k}{B}}$$

$$\text{Or } \ln\left(\frac{MIC}{C_0}\right) + \frac{k}{2}\ln(\pi) + \frac{k}{2}\ln(B) + \frac{r^k}{B} = 0$$

Once the k and B are known per tested antibiotic, an estimation of the concentration of every antibiotic in the media can be estimated as a function of distance to the source disk (knowing its initial concentration $C_0$) to produce suitable distance maps for various disks. Thus, the growth modulation may be estimated (modelled) as a function of distance to each antibiotic disk. Moreover, optionally, the growth modulation may be estimated (modelled) as a function of antibiotic estimated concentration.

Image Comparison and Contrast

In the aforementioned processes, determining whether growth exists in relation to the disks of the plates may be implemented from comparing images (observed at time $t_0$-to-observed at time $t_x$ and/or observed-to-simulated) to determine contrast therebetween. In this regard, over time, bacteria on an AST plate will grow. The earlier in time from when the bacteria are placed in the plate, the less bacteria there is to detect and, consequently there is lower contrast to the background. Stated another way, a smaller colony size yields a smaller signal, and a smaller signal on a constant background results in smaller contrast. This is reflected by the following equation:

$$\text{Contrast} = \frac{\text{Signal} - \text{background}}{\text{Signal} + \text{background}} \quad (1)$$

Contrast can play an important role in identifying growth objects in the images. An object can be detected in an image if it is significantly different in brightness, color and/or texture from its surroundings. Once an object has been detected, the analysis may also involve identifying the type of object that has been detected. Such identifications can also rely on contrast measurements, such as the smoothness of edges of the identified object, or the uniformity (or lack of uniformity) of the color and/or brightness of the object. This contrast must be great enough to overcome the image noise (background signals) to be detected by the image sensor.

The human perception of contrast (governed by Weber's law) is limited. Under optimal conditions, human eyes can detect a light level difference of 1%. The quality and confidence of image measurements (e.g., brightness, color, contrast) may be characterized by a signal-to-noise ratio (SNR) of the measurements, in which an SNR value of 100 (or 40 db), independent from pixel intensities, would match human detection capabilities. Digital imaging techniques utilizing high SNR imaging information and known SNR per pixel information can allow for detection of colonies even when those colonies are not yet visible to human eyes.

However, visually observable or visually perceivable contrast does not necessarily mean that the observed temporal contrast, in and of itself, is a reliable determination of microbial growth modulation in the vicinity of an antibiotic disk. Because the present method can determine the extent of temporal contrast, the present method can provide an indication to the user whether or not the observed temporal contrast is adequate for a reliable determination of microbial modulation by setting a threshold amount of temporal contrast (i.e., 1% or more, 2% or more, 3% or more, 4% or more, 5% or more, etc.) required before the user is provided an indication that a reliable determination of microbial growth can now be made. The selected threshold will vary based on the type of nutrient media (e.g. Mueller Hinton Agar (MH), Mueller Hinton Agar with 5% Sheep Blood, Mueller Hinton Chocolate Agar, etc.) and the type of microorganism (e.g. *Neisseria* or *Haemophilus* sp., *N. gonorrhoeae*, *E. coli*, *Salmonella*, *Shigella*, *Staphylococcus aureus*, etc.). Typically, a higher amount of contrast is required when lighter colonies form on lighter agars (e.g., MH) or darker colonies of similar color form on darker agars (e.g. MH Chocolate Agar). It is therefore contemplated that the extent of temporal contrast required for a reliable determination of microbial growth modulation will be set at different thresholds for different combinations of agar and microorganisms. Once the extent of measured temporal contrast is detected that meets or exceeds the set threshold, the user will be notified that the plate is ready for analysis. If the extent of measured temporal contrast does not meet or exceed the specified threshold, then the user is advised to continue to incubate the sample for another cycle or invalidate the sample due to poor sample quality. This is advantageous because, while a skilled user can perceive contrast, the skilled user can perceive growth, the skilled user cannot always visually discern accurately a 50% or 80% modulation of the growth from an observed change in intensity (when the absolute difference is between a 2% difference in intensity and a 3% difference in intensity), leading to an erroneous read of the inhibition region around a given antibiotic disk.

In the present disclosure, contrast may be collected in at least two ways: spatially and temporally. Spatial contrast, or local contrast, quantifies the difference in color or brightness between a given region (e.g., pixel, group of adjacent pixels) and its surroundings in a single image. Temporal contrast, or time contrast, quantifies the difference in color or brightness between a given region of one image against that same region in another image taken at a different time. The formula governing temporal contrast is similar to that for spatial contrast:

$$\text{Temporal Contrast} = \frac{|\text{Signal}(t_1) - \text{Signal}(t_2)|}{\text{Signal}(t_1) + \text{Signal}(t_2)} \quad (2)$$

In which $t_2$ is a time subsequent to $t_1$. Both spatial and temporal contrasts of a given image may be used to identify growth.

To maximize spatial or temporal contrast of an object against its background, the system may capture images using different incident lights on different backgrounds. For instance, any of top lighting, bottom lighting, or side lighting may be used on either a black or white background.

At a given point in time, multiple images may be captured under multiple illumination conditions. Images may be captured using different light sources that are spectrally different due to illumination light level, illumination angle, and/or filters deployed between the object and the sensor (e.g. red, green and blue filters). In this manner, the image acquisition conditions may be varied in terms of light source position (e.g., top, side, bottom), background (e.g., black, white, any color, any intensity), and light spectrum (e.g. red channel, green channel, blue channel). For instance, a first image may be captured using top illumination and a black background, a second image captured using side illumination and a black background, and a third image captured using bottom illumination and no background (i.e. a white background). Furthermore, specific algorithms may be used to create a set of varying image acquisition conditions to maximize spatial contrast using. These or other algorithms can also be useful to maximize temporal contrast by varying the image acquisition conditions according to a given sequence and/or over a span of time. Some such algorithms are described in PCT Publication No. WO2015/114121.

Contrast information between two images may be determined. The contrast information may be gathered on a pixel-by-pixel basis. For example, the pixels of the second digital image may be compared with the corresponding pixels (at the same coordinates) of the first digital image to determine the presence of temporal contrast. Additionally, adjacent pixels of the second digital image may be compared with one another, or with other pixels known to be background pixels, to determine the presence of spatial contrast. Changes in pixel color and/or brightness are indicative of contrast, and the magnitude of such changes from one image to the next or from one pixel (or region of pixels) to the next, may be measured, calculated, estimated, or otherwise determined. In cases where both temporal contrast and spatial contrast is determined for a given image, an overall contrast of a given pixel of the image may be determined based on a combination (e.g., average, weighted average) of the spatial and temporal contrasts of that given pixel.

Growth in the second digital image may be identified based on computed contrast information. Adjacent pixels of the second digital image having similar contrast information may be considered to belong to the same growth. For instance, if the difference in brightness between the adjacent pixels and their background, or between the pixels and their brightness in the first digital image, is about the same (e.g., within a predetermined threshold amount), then the pixels may be considered to belong to the same growth object. As an example, the system could assign a "1" to any pixel having significant contrast (e.g., over the threshold amount), and then identify a group of adjacent pixels all assigned "1" as a growth object. The object may be given a specific label or mask, such that pixels with the same label share certain characteristics. The label can help to differentiate the growth from other objects (e.g., disks) and/or background during later processes.

Identifying objects in a digital image may involve segmenting or partitioning the digital image into multiple regions (e.g., foreground and background). The goal of segmentation is to change the image into a representation of multiple components so that it is easier to analyze the components. Image segmentation is used to locate objects of interest in images such as antibiotic disks.

The use of such automated processes may allow for faster AST testing. Such testing in an automated process can begin soon after the initial placement of AST disks, and the results may be obtained and reported more rapidly. By contrast, such testing in a manual process often takes additional time to complete before the data can be reviewed and reported. Thus, the automated process of the present disclosure, aided with the modeling and/or contrast processing described herein, may provide for faster testing without adversely affecting the quality or accuracy of the test results.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method in a processor for antibiotic susceptibility testing comprising:
   providing a culture plate inoculated with a biological sample, the culture plate having culture media and at least one antibiotic disk disposed thereon;
   receiving first and second image data of the culture plate generated with an image sensor and wherein the first image data serves as a pre-growth reference, the first image data and second image data respectively representing first and second captured images of the culture plate having a plurality of antibiotic disks thereon, the first and second captured images taken at separate times,
   generating pixel characteristic data for pixels of the second image data from a comparison of the first image data and the second image data, the pixel characteristic data indicative of microbial growth on the culture plate over time;
   accessing growth modeling data for microbial growth, wherein the growth modeling data models microbial growth for combinations of culture media, microorganisms, antibiotic, antibiotic concentration on at least one antibiotic disk of the plurality of antibiotic disks and in the culture media wherein the antibiotic concentration in the culture media is a function of antibiotic concentration on the antibiotic disk, time and a distance from the antibiotic disk;
   generating simulated image data with a growth model function, the growth model function using the growth modeling data, the simulated image data simulating microbial growth on the inoculated culture plate based on the at least one antibiotic disk of the plurality of antibiotic disks disposed on the culture media, the antibiotic concentration on the at least one antibiotic disk; the culture media and the antibiotic concentration in the culture media as a function of time and distance from the antibiotic disk; and
   comparing the simulated image data and the pixel characteristic data and identifying one or more pixel regions of the second image data that differ from one or more pixel regions of the simulated image data.

2. The method of claim 1, wherein the generated pixel characteristic data comprises contrast data.

3. The method of claim 2, wherein the contrast data comprises pixel intensity values.

4. The method of claim 3, wherein the contrast data further comprises one or more of opacity data, color data and blurring data.

5. The method of claim 1, wherein the pixel characteristic data comprises distance data, the distance data representing distance to the at least one of the plurality of antibiotic disks.

6. The method of claim 5, wherein the distance data comprises a distance to center of the at least one of the plurality of antibiotic disks.

7. The method of claim 1, wherein the growth model function comprises a maximum growth model, a minimum growth model, an average growth model, a median growth model or a percentile growth model.

8. The method of claim 1, wherein the growth model function characterizes contrast data as a function of radial distance from the at least one antibiotic disk of the plurality of antibiotic disks.

9. The method of claim 1, wherein the growth model function comprises a diffusion map.

10. The method of claim 1, further comprising:
    detecting in the first image data or second image data, antibiotic disk image data of the at least one antibiotic disk of the plurality of antibiotic disks,
    analyzing the antibiotic disk image data to detect indicia data; and
    wherein the step of accessing growth modeling data comprises locating the growth modelling data using the indicia data.

11. The method of claim 1, wherein the growth modelling data comprises concentration information for an antibiotic load of the at least one antibiotic disk of the plurality of antibiotic disks.

12. The method of claim 1, wherein the growth model function uses a growth time parameter representing elapsed time for microbial growth on the culture plate at a time of capture of the second image data.

13. The method of claim 1, wherein the growth model function uses a diffusion coefficient parameter.

14. The method of claim 1, wherein the growth model function uses a dimensionality parameter.

15. The method of claim 1, wherein the generated simulated image data comprises an image mask having first image pixels representing a no-growth zone corresponding with a location of the at least one antibiotic disk of the plurality of antibiotic disks on the culture plate and second image pixels representing a growth zone radiating from the no-growth zone and beginning at a radial distance from the location, the radial distance determined from the growth model function, the radial distance representing an estimated inhibition zone limit for the at least one antibiotic disk.

16. The method of claim 15, wherein the comparing the simulated image data and the pixel characteristic data comprises contrasting the image mask and the pixel characteristic data to generate difference image data.

17. The method of claim 16, further comprising evaluating a region of the second image data based on the difference image data.

18. The method of claim 1, wherein the first image data serves as a pre-growth reference.

19. The method of claim 1, further comprising controlling the image sensor to capture the first and second captured images of the culture plate.

20. The method of claim 2, wherein the contrast data comprises temporal contrast data and spatial contrast data.

21. The method of claim 20, further comprising:
setting a threshold temporal contrast value as an indication of modulation of microbial growth caused by the antibiotic disk; and
when a measured temporal contrast between one or more pixels in the first image data and one or more pixels in the second image data exceeds the threshold temporal contrast value, providing an indication to a user that the second captured image can be used evaluate microbial growth; or
when the measured temporal contrast between one or more pixels in the first image data and one or more pixels in the second image data does not exceed the threshold temporal contrast value, providing an indication to a user that the second captured image cannot be used to evaluate microbial growth.

22. The method of claim 21, further comprising:
in response to the indication that the second image data cannot be used to evaluate microbial growth, either: i) further incubating the culture plate for an additional period of time after the second captured image was obtained;
when the additional period of time has elapsed, receiving third image data of the culture plate generated with the image sensor, the third image data representing a third captured image of the culture plate including the plurality of antibiotic disks;
generating pixel characteristic data for pixels of the third image data from a comparison of the second image data and the third image data, the pixel characteristic data indicative of microbial growth on the culture plate over time;
accessing growth modeling data for microbial growth, wherein the growth modeling data models microbial growth for combinations of culture media, microorganisms, antibiotic, antibiotic concentration on the at least one of the plurality of antibiotic disks and in the culture media;
generating simulated image data with the growth model function; and
comparing the simulated image data and the pixel characteristic data and identifying one or more pixel regions in the third image data that differ from one or more pixel regions of the simulated image data; or
ii) provide a signal to invalidate the biological sample.

23. A non-transitory computer medium containing programming instructions that when executed by a processor control the processor for antibiotic susceptibility testing, wherein the programming instructions control the processor to perform the method of claim 1.

24. A system for antibiotic susceptibility testing comprising:
an image sensor configured to capture images of a culture plate on which is disposed culture media with at least one antibiotic disk disposed thereon, wherein the culture plate is inoculated with a biological sample wherein the culture plate is within a field of view of the image sensor;
a processor coupled with the image sensor; and
a non-transitory computer medium containing programming instructions that when executed by the processor control the processor for testing antibiotic susceptibility, wherein the program instructions control the processor to perform the method of claim 1.

25. A system for antibiotic susceptibility testing comprising:
an image sensor configured to capture images of a culture plate on which is disposed culture media with a plurality of antibiotic disks disposed thereon, wherein the culture plate is inoculated with a biological sample when the culture plate is within a field of view of the image sensor, the image sensor generating first image data and second image data, the first image data and second image data respectively representing first and second captured images of the culture plate including the plurality of antibiotic disks, the first and second captured images taken at different times and wherein the first image data serves as a pre-growth reference;
a processor and a memory, the processor configured to receive the first image data and second image data and access the memory, the memory storing growth modeling data;
wherein the processor is configured to:
receive the first image data and the second image data,
generate pixel characteristic data for pixels of the second image data from a comparison of the first image data and the second image data, the pixel characteristic data indicative of microbial growth on the culture plate;
access growth modeling data, wherein the growth modelling data models microbial growth as a function of culture media, microorganism, antibiotic and antibiotic concentration;
generate simulated image data with a growth model function, the growth model function using the growth modeling data, the simulated image data simulating microbial growth on the culture plate in relation to at least one disk of the plurality of antibiotic disks; and
compare the simulated image data and the pixel characteristic data to identify one or more pixel regions of the second image data that differ from the simulated image data.

* * * * *